(12) United States Patent
Stiles et al.

(10) Patent No.: US 9,366,686 B2
(45) Date of Patent: Jun. 14, 2016

(54) MICROPLATE STACKER FOR PLATES WITH LIDS

(71) Applicant: BioTek Instruments, Inc., Winooski, VT (US)

(72) Inventors: Matthew Stiles, Montpelier, VT (US); William David Nicolay, N. Ferrisburgh, VT (US); G. Gerard Gormley, Worcester, VT (US); Byron Smith, South Hero, VT (US)

(73) Assignee: BIO-TEK INSTRUMENTS, INC., Winooski, VT (US)

( * ) Notice: Subject to any disclaimer, the term of this patent is extended or adjusted under 35 U.S.C. 154(b) by 0 days.

(21) Appl. No.: 14/517,200

(22) Filed: Oct. 17, 2014

(65) Prior Publication Data

US 2015/0110690 A1    Apr. 23, 2015

Related U.S. Application Data

(60) Provisional application No. 61/892,930, filed on Oct. 18, 2013.

(51) Int. Cl.
*B01L 9/00* (2006.01)
*G01N 35/04* (2006.01)

(52) U.S. Cl.
CPC ........ *G01N 35/04* (2013.01); *G01N 2035/0425* (2013.01)

(58) Field of Classification Search
CPC ..... B01L 9/52; B01L 9/523; G01N 2035/014; G01N 2035/0425
USPC ........................... 422/560–561, 563, 62–68.1
See application file for complete search history.

(56) References Cited

U.S. PATENT DOCUMENTS 5,985,214 A * 11/1999  Stylli et al. ...................... 422/65

* cited by examiner

*Primary Examiner* — Brian R Gordon
(74) *Attorney, Agent, or Firm* — Sughrue Mion, PLLC

(57) ABSTRACT

A microplate stacker capable of removing and replacing standard microplate lids by separating a microplate from a lid located directly above the microplate in a stack of microplates and lids.

7 Claims, 26 Drawing Sheets

MICROPLATE STACKER FOR PLATES WITH LIDS

CROSS-REFERENCE TO RELATED APPLICATION

This application is a non-provisional application of U.S. Provisional Application No. 61/892,930 filed on Oct. 18, 2013, in the U.S. Patent and Trademark Office, the disclosures of which is incorporated by reference in its entirety.

BACKGROUND

1. Field

Methods and apparatuses consistent with embodiments relate to a microplate stacker, and more particularly to a microplate stacker, for microplates with lids, that is capable of extracting standard microplates with lids from the bottom of a stack of microplates and lids, as necessary for processing and stacking the microplates and lids.

2. Description of Related Art

The American National Standards Institute (ANSI) has published a standard generated by the Society for Laboratory Automation and Screening (SLAS), ANSI/SLAS 1-2004, which describes standard microplate dimensions.

FIG. 1 illustrates a microplate 1 including wells 2, according to the ANSI/SLAS 1-2004 standard. The microplate 1 illustrated in FIG. 1 includes 96 wells 2, but the quantity of wells 2 may differ according to the format of the microplate 1.

Microplate manufacturers typically provide one or more standard lid types that are compatible with the manufacturer's microplates. The purpose of the microplate lid is to protect the contents in the microplate wells from external contamination, from cross contamination between the wells, and to limit evaporation of fluid from the wells. Well contamination is of particular concern when working with live organic cells.

FIG. 2 illustrates a microplate 1 having a lid 3 according to the ANSI/SLAS 1-2004 standard and Microplate Footprint Dimensions. As illustrated in FIG. 2, the lid 3 is configured to be seated on top of the microplate 1.

FIG. 3 illustrates a stack of microplates 1 and lids 3 according to the ANSI/SLAS 1-2004 standard and Microplate Footprint Dimensions.

As illustrated in FIG. 3, in addition to being seated on top of its microplate 1, the lid is further configured to act as a base upon which a next microplate 1 is to be nested in the stack of microplates 1 and lids 3. By stacking the microplates and lids, the microplates and lids may be efficiently processed and stored.

Microplates may be processed in a variety of laboratory instruments, such as liquid dispensers, washers, and readers. A "stacker" is one such automated system.

FIG. 4 illustrates a conventional stacker.

As illustrated in FIG. 4, the conventional stacker includes a stack of microplates 4 stored in a source cassette 5. The microplates in the stack of microplates 4 may be individually removed from the cassette 5, typically from the bottom of the source cassette 5. The microplate removed from the stack of microplates 4 may then be presented to a laboratory instrument for processing. After processing, the stacker stores the microplate in a destination cassette 7 for stacking processed microplates.

Microplate "stackers" are commonly available. Examples include the BIOTEK BIOSTACK and TECAN CONNECT MICROPLATE STACKER. Stackers are characterized by the ability to load and unload microplates from the bottom of the stack, and are typically more compact and lower cost than the more sophisticated automatic systems. Such stackers, however, are incapable of removing and replacing microplate lids.

Conventional stackers generally work under the following principle characteristics, which will be discussed with reference to FIGS. 5 to 10.

As illustrated in FIG. 5, a stack of microplates 4 is loaded into a cassette 8, sliding down to the bottom of the cassette 8 by gravity, with the lowermost microplate resting upon support features 9 located at the base of the cassette 8.

The support features 9 may be positioned on inner peripheral edges of a wall of the cassette 8, as illustrated in FIG. 5.

As illustrated in FIG. 6, a lift mechanism 10 may be disposed beneath the support features 9 for raising and lowering the stack of microplates 4 loaded into the cassette 8.

As illustrated in FIG. 7, in operation, the lift mechanism 10 lifts the lowermost microplate, and thus all microplates in the stack of microplates 4, off of the support features 9. The lift mechanism 10 may be disposed on an inner central portion of the cassette 8. Once the lift mechanism 10 has lifted the stack of microplates 4, the support features 9 are retracted. The support features 9 may be retracted by cam motion 11 or any actuating mechanism, motor, etc.

As illustrated in FIG. 8, the lift mechanism 10 is lowered a predetermined distance such that the support features 9 are aligned with a gap ($\alpha$) that exists between the bottom flange of the lowermost microplate, and the bottom of the microplate above the lowermost microplate.

As illustrated in FIG. 9, once the support features 9 are positioned by the lift mechanism 10, the support features 9 are extended.

The gap ($\alpha$) into which the support features 9 extend is typically 4 mm to 12 mm.

As illustrated in FIG. 10, the lift mechanism 10 is lowered. Accordingly, the lowermost microplate 1 is lowered and separated from the stack of microplates 4, while the remaining microplates remain in the stack of microplates 4 due to support by the support features 9.

Once removed from the stack of microplates 4, the microplate is then passed to an attached laboratory instrument through any combination of conveyors, articulating robots, etc.

A shortcoming of the conventional stacker described above is that, when processing microplates with lids, there is minimal or no spacing 11 between the lid of the lowermost microplate, and the base of the microplate above the lowermost microplate. Accordingly, the support feature cannot reliably be extended to support a selected microplate, as illustrated in FIG. 11. Removal of microplates from the stack of microplates, therefore, becomes difficult or impossible.

To solve the aforementioned shortcomings, a microplate lid described by U.S. Pat. No. 6,254,833 proposes a lid with recesses in the sides, whereby a lid may be separated from its microplate within a stacker with elevator, by use of support features within the stack. A drawback of the design is that the user is limited to a specific microplate and lid manufacturer.

Alternatively, microplate "delidders" are commonly available. The THERMO SCIENTIFIC MICROPLATE DELIDDER is one such example. Separate delidder stations of this type are commonly part of a larger automated system including an articulating robot (i.e. a robot capable of reaching multiple stations—plate storage stations, delidder, and laboratory instruments). The drawback of such a system is the added expense, complexity, and size of the multiple components, particularly when used in small and medium sized laboratories.

Automated robot systems capable of removing microplate lids are also commonly available. The HUDSON ROBOTICS PLATECRANE EX is one example. Such systems typically include an articulating robot that uses a gripper mechanism to retrieve microplates from the top of a stack of microplates. The robot typically includes a vacuum suction cup, gripper, or other mechanism to lift the lid from the microplate (delid the microplate). The drawback of such a system is the added expense, complexity, and size of the robotic system.

It is therefore an objective of the present application to provide a microplate stacker with integrated capability to remove and replace standard microplate lids. As a result, the aforementioned drawbacks of conventional stackers, delidders, and automated systems may be overcome.

SUMMARY

Embodiments described herein overcome the above disadvantages and other disadvantages not described above. Also, the embodiments are not required to overcome the disadvantages described above, and an embodiment may not overcome any of the problems described above.

According to an aspect of an embodiment, there is provided a microplate stacker including a cassette stack configured to stack a plurality of microplates and a plurality of lids corresponding to the plurality of microplates, a lift mechanism configured to raise or lower the stack of the plurality of microplates and the plurality of lids, and a stack dog configured to separate a microplate among the plurality of microplates from a lid among the plurality of lids that corresponds to the microplate.

DETAILED DESCRIPTION OF EMBODIMENTS

Figure 1:
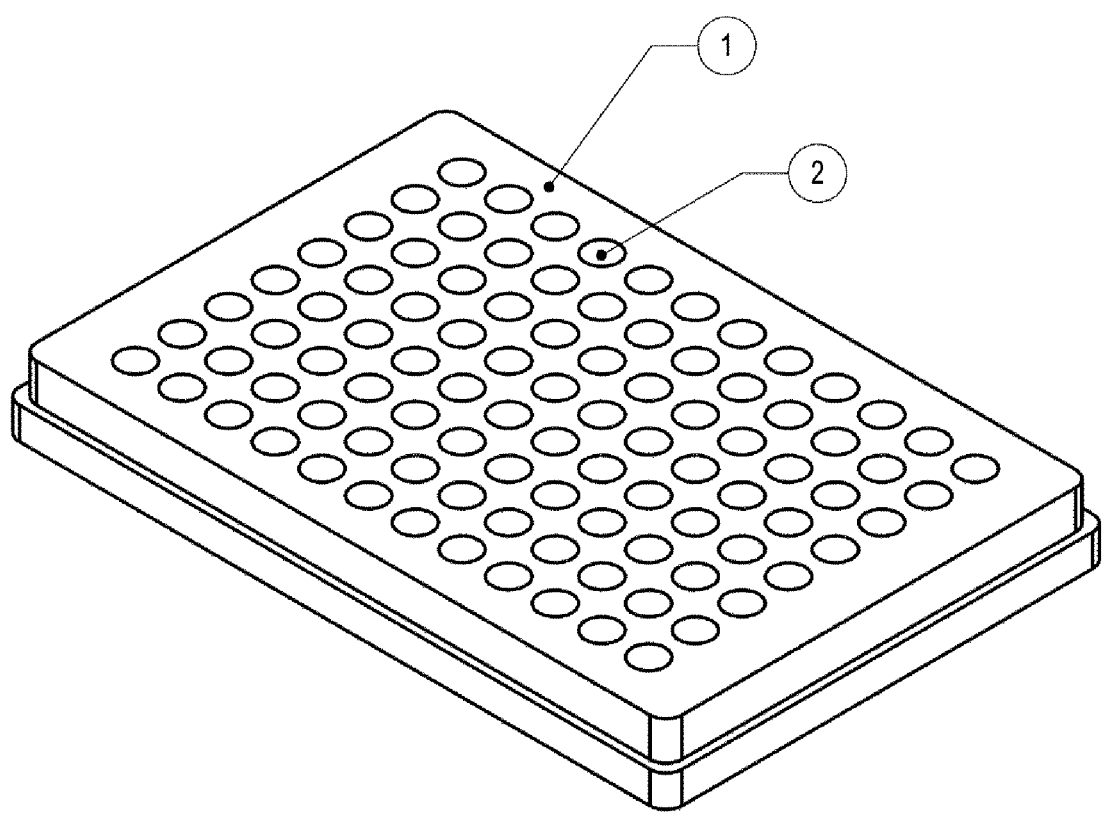
FIG. 1 illustrates a conventional microplate.
Figure 2:
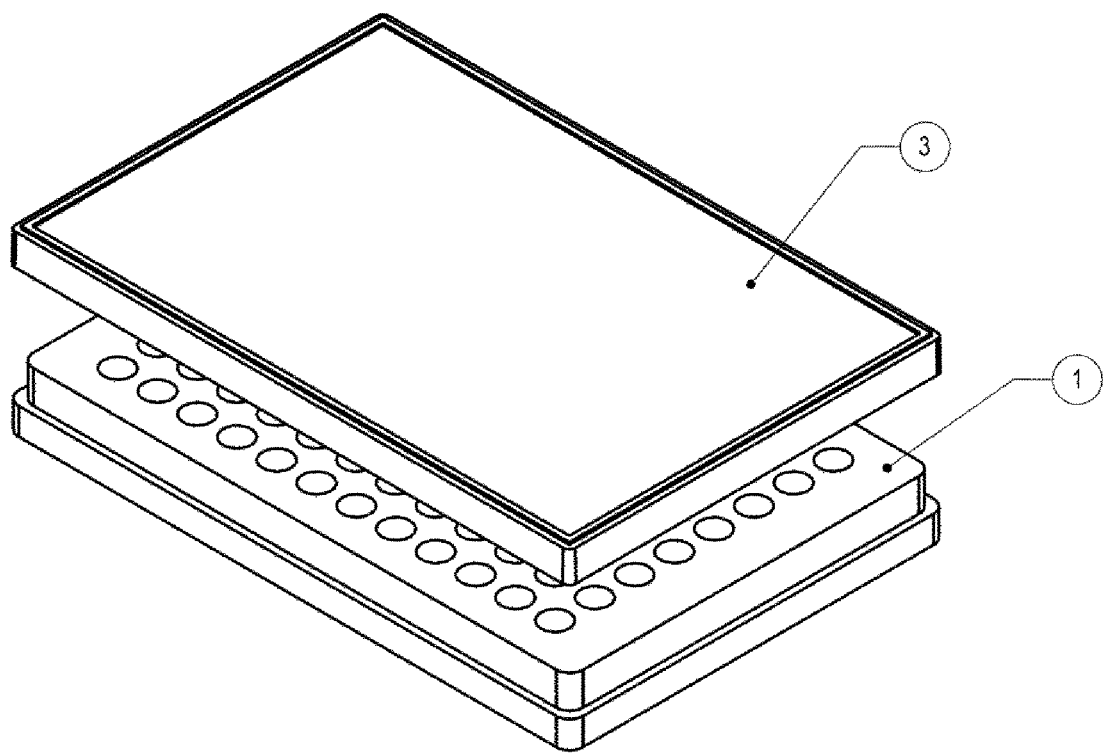
FIG. 2 illustrates a conventional microplate and lid.
Figure 3:
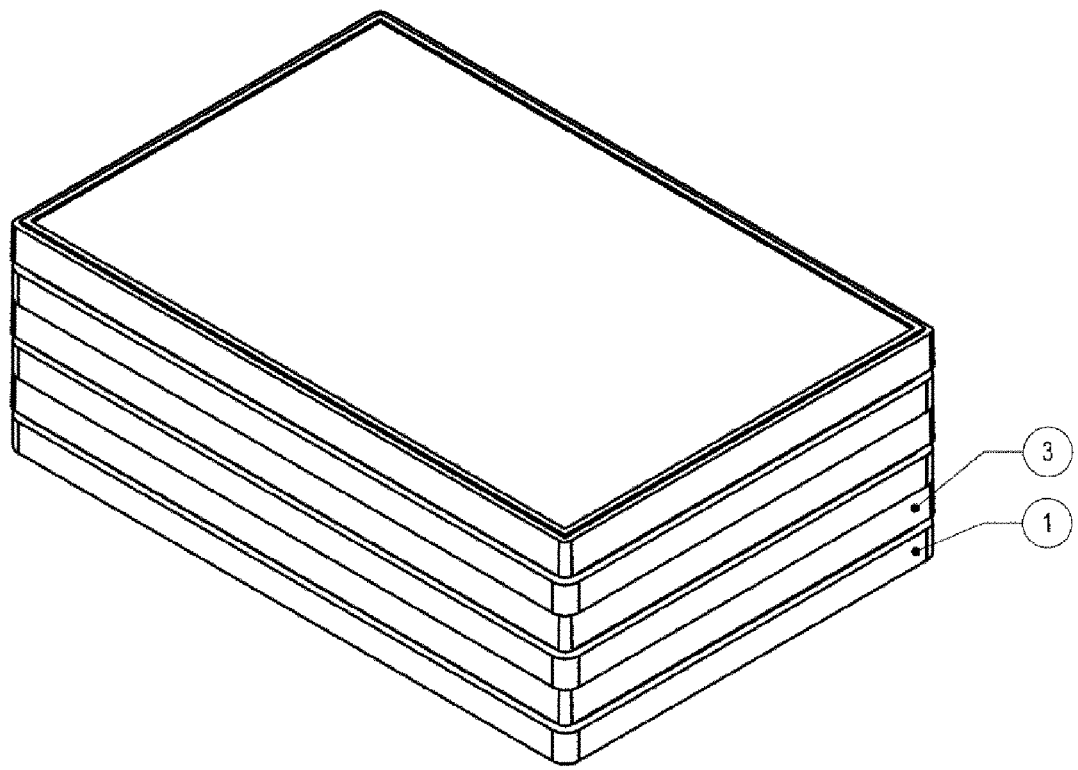
FIG. 3 illustrates a conventional stack of microplates and lids.
Figure 4:
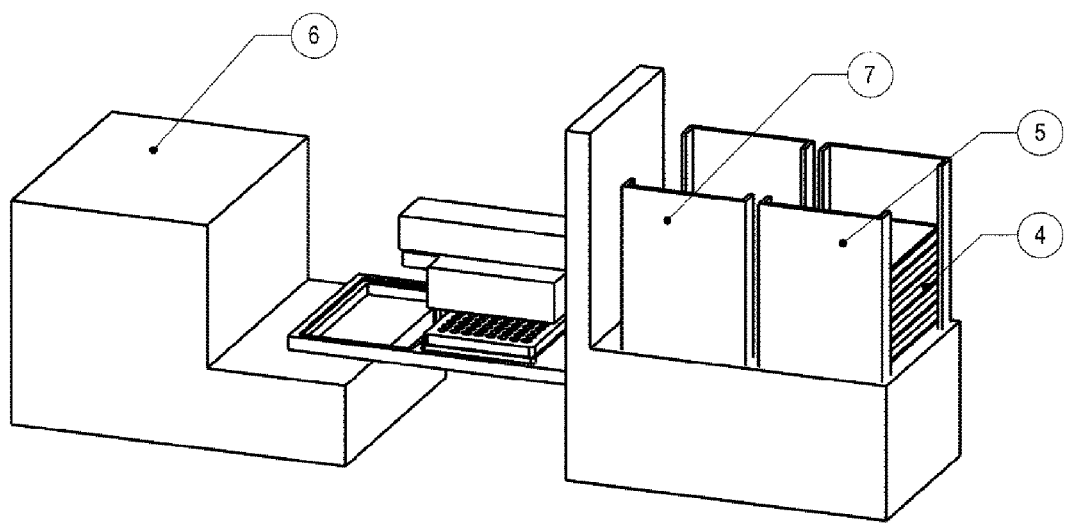
FIG. 4 illustrates a conventional stacker.
Figure 5:
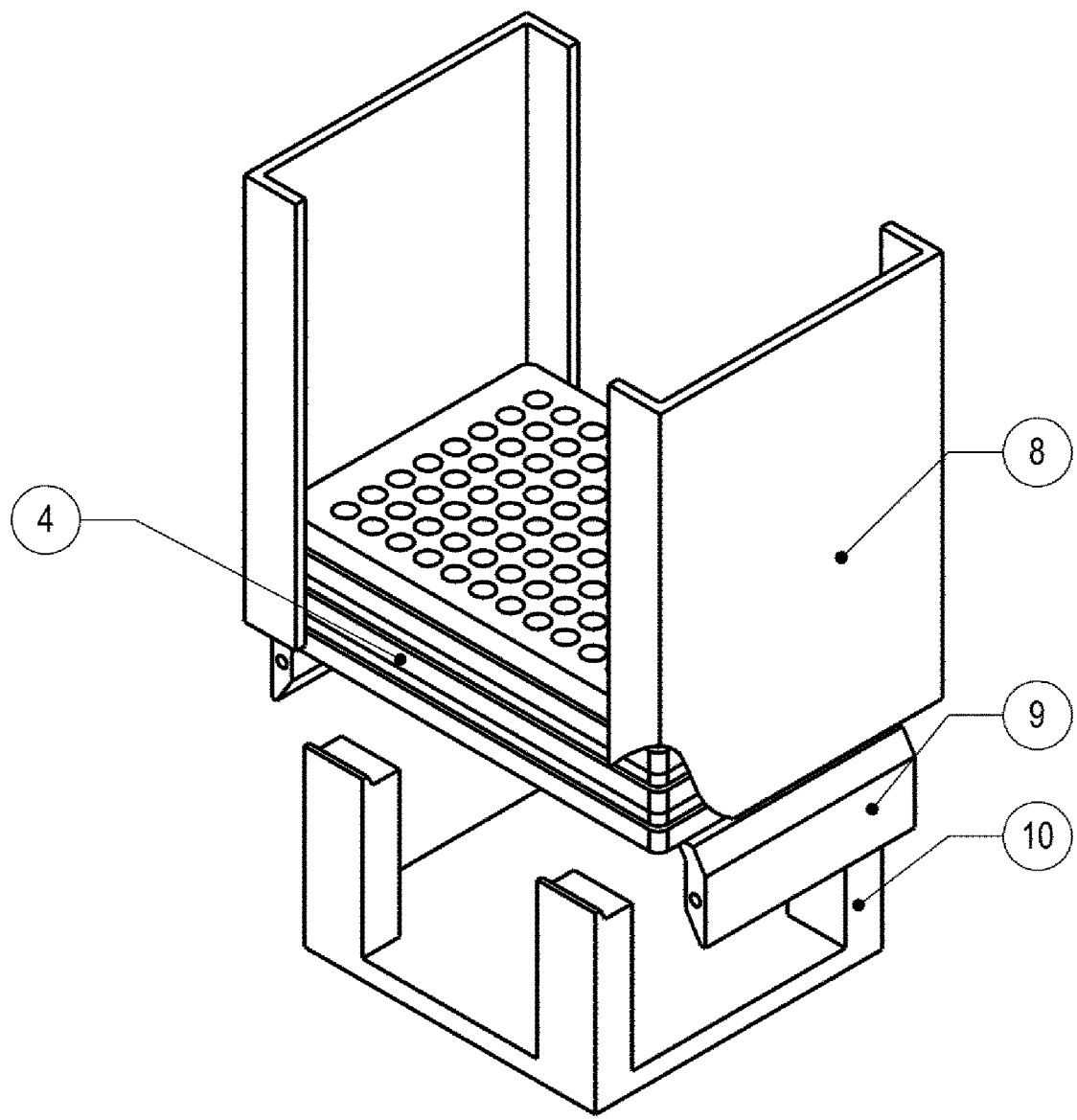
FIGS. 5-10 illustrate operations of a conventional stacker.
Figure 6:
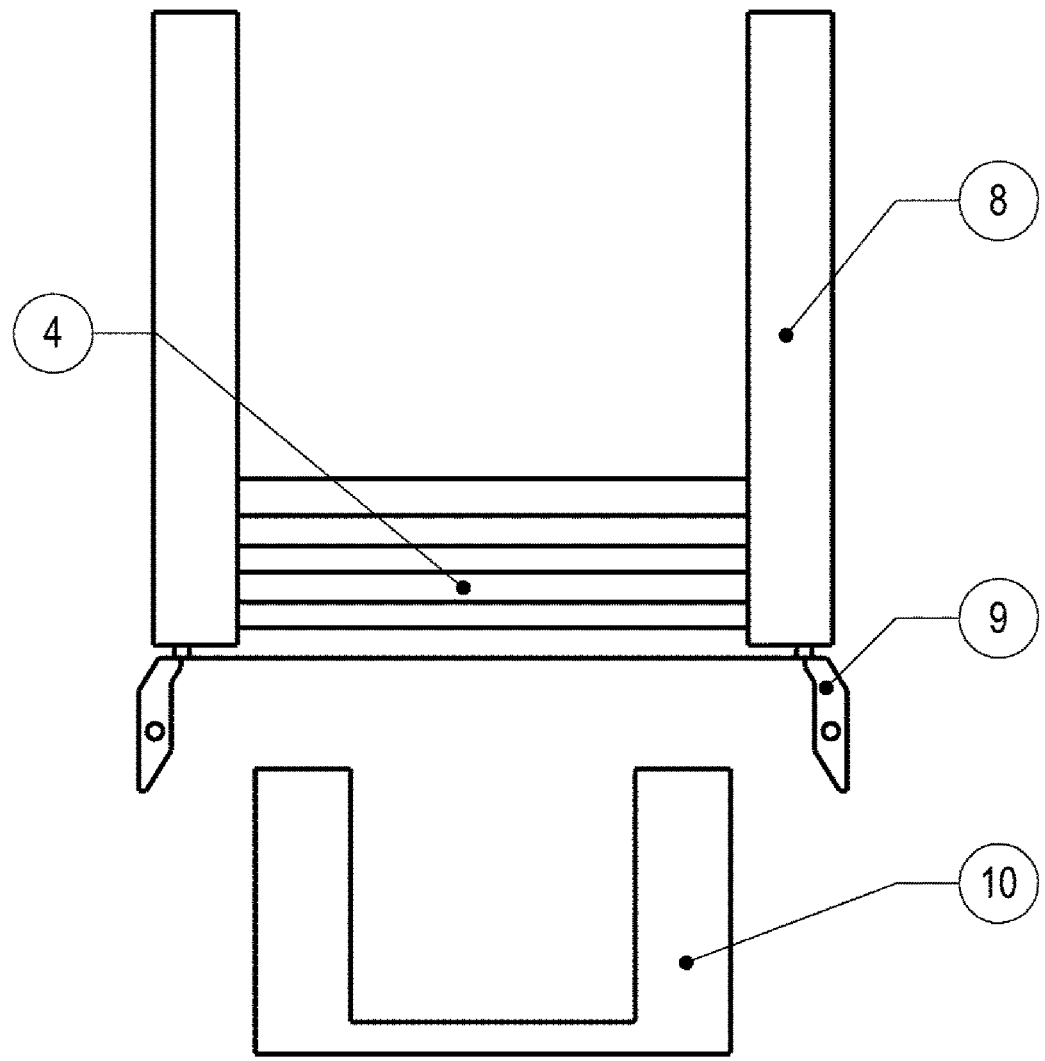
Figure 7:
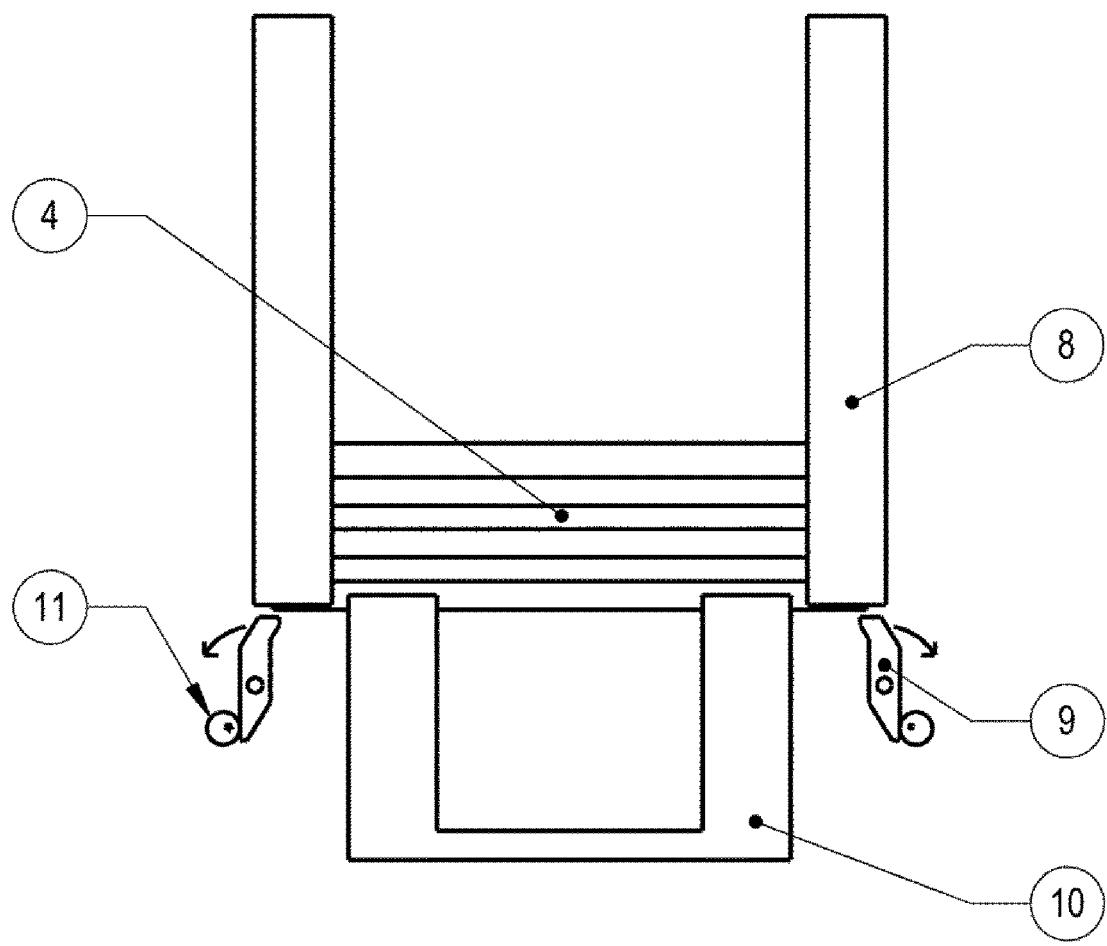
Figure 8:
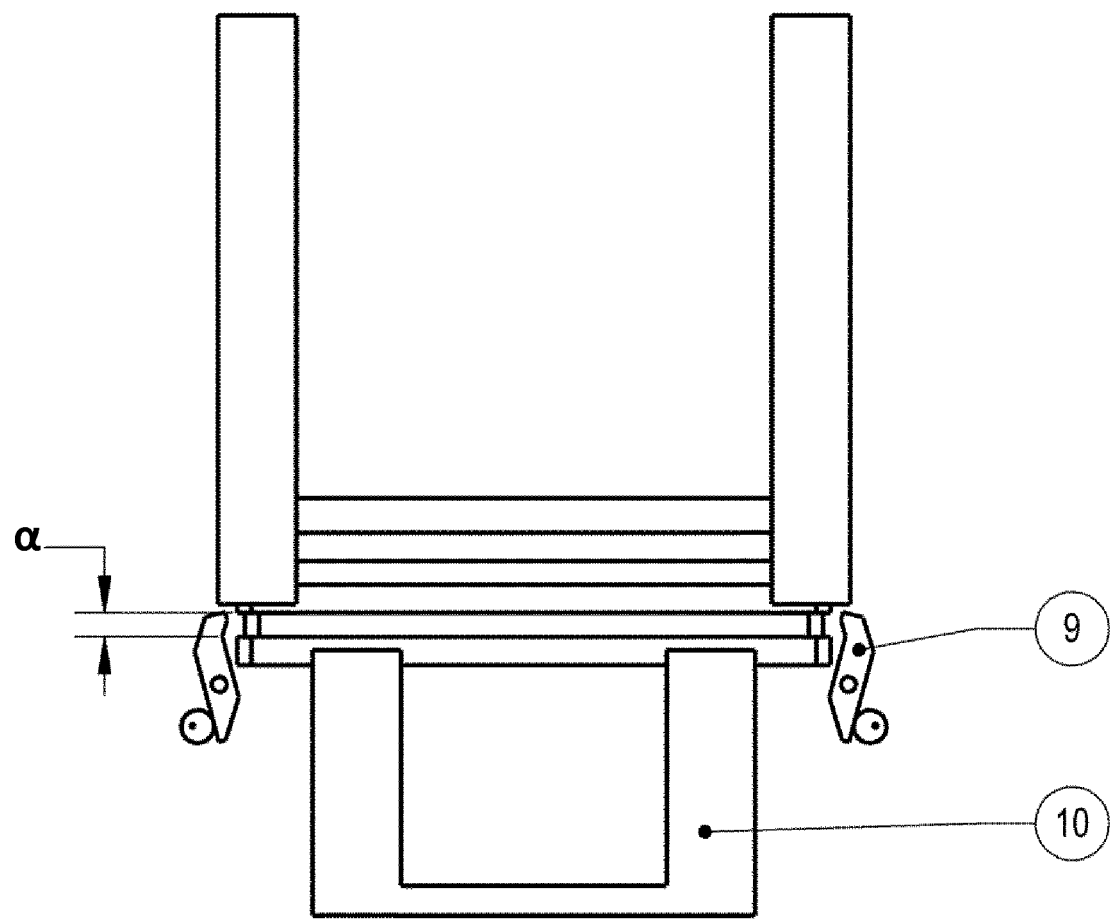
Figure 9:
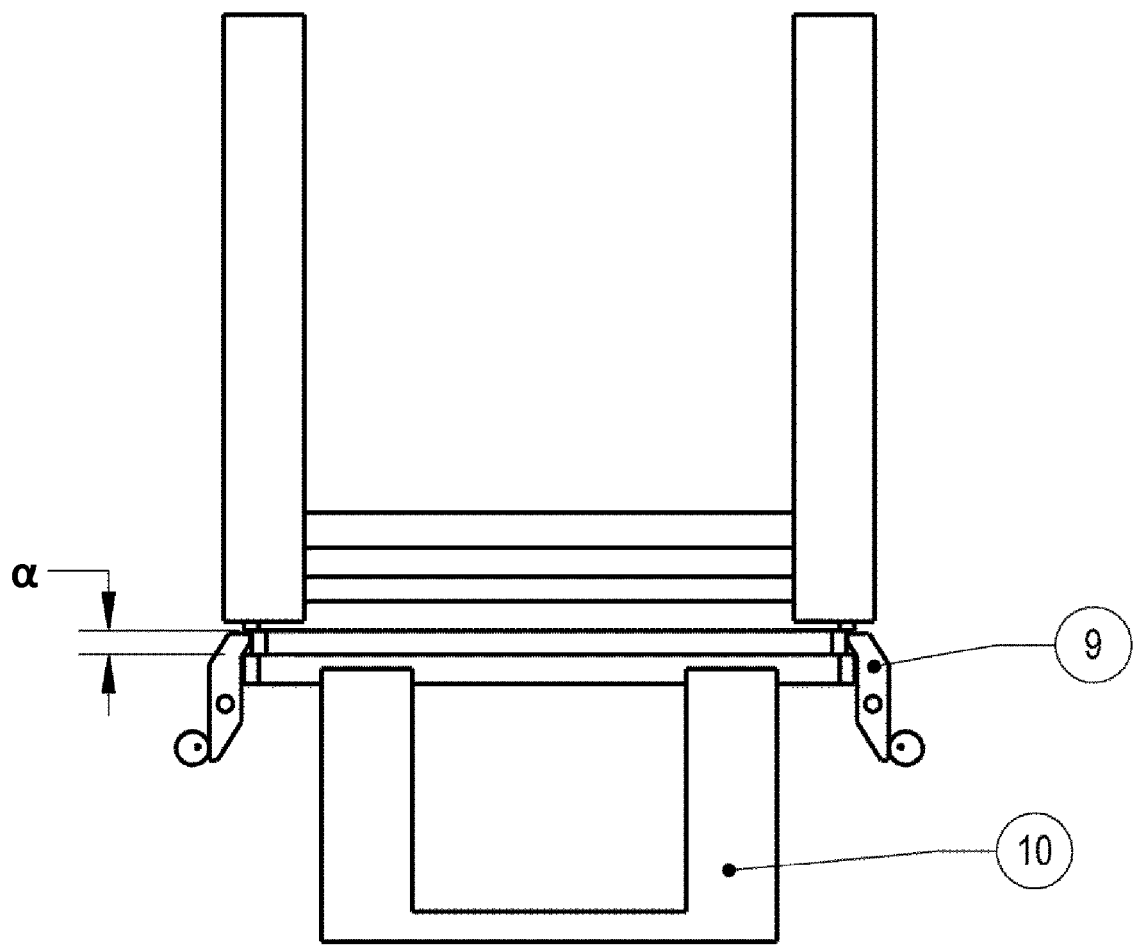
Figure 10:
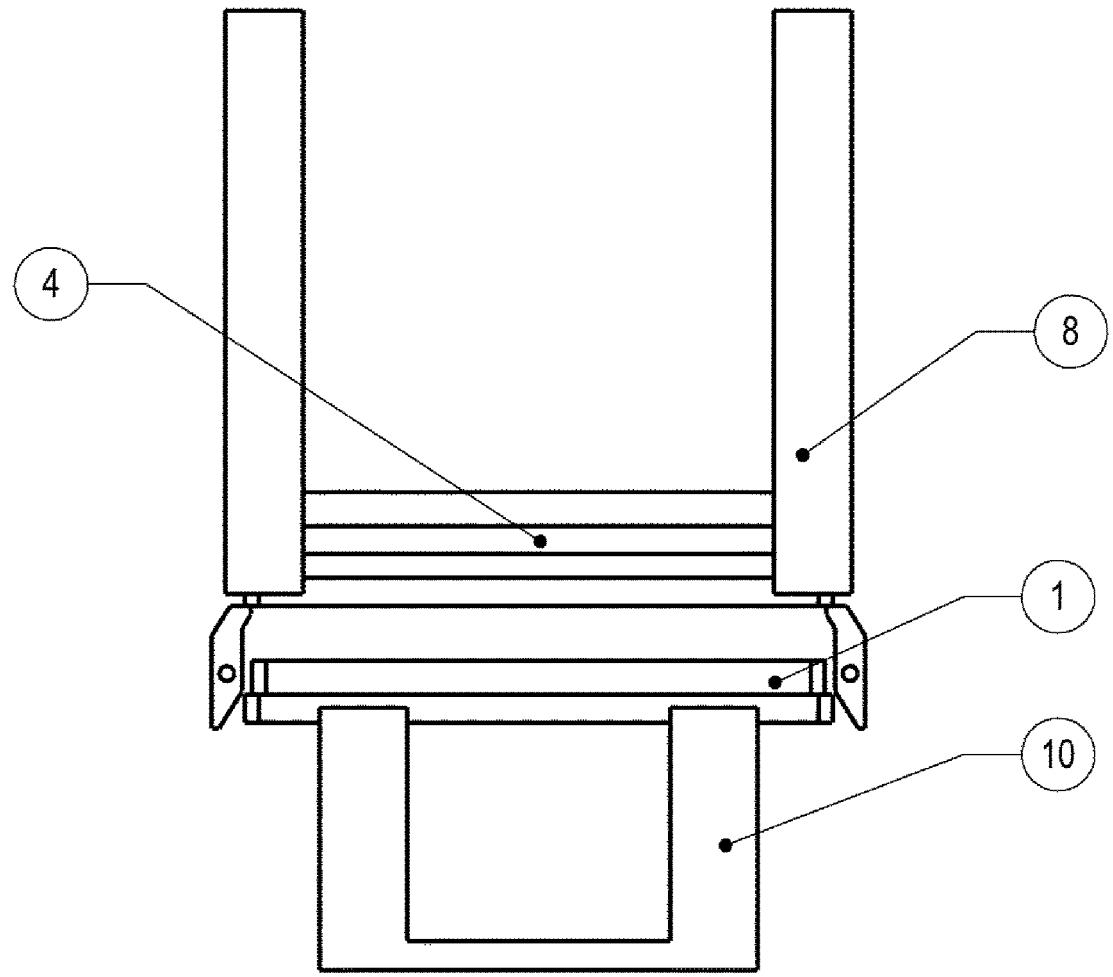

Hereinafter, embodiments will be described in detail with reference to the accompanying drawings. The aspects and features of the embodiments and methods for achieving the aspects and features will be apparent by referring to the embodiments to be described in detail with reference to the accompanying drawings. However, the embodiments are not limited to the embodiments disclosed hereinafter, but can be implemented in diverse forms. The matters defined in the description, such as details of construction and elements, are only provided to assist those of ordinary skill in the art in a comprehensive understanding of the disclosure, and the present disclosure is only defined within the scope of the appended claims. In the entire description, the same drawing reference numerals are used for the same elements across various figures.

Figure 12:
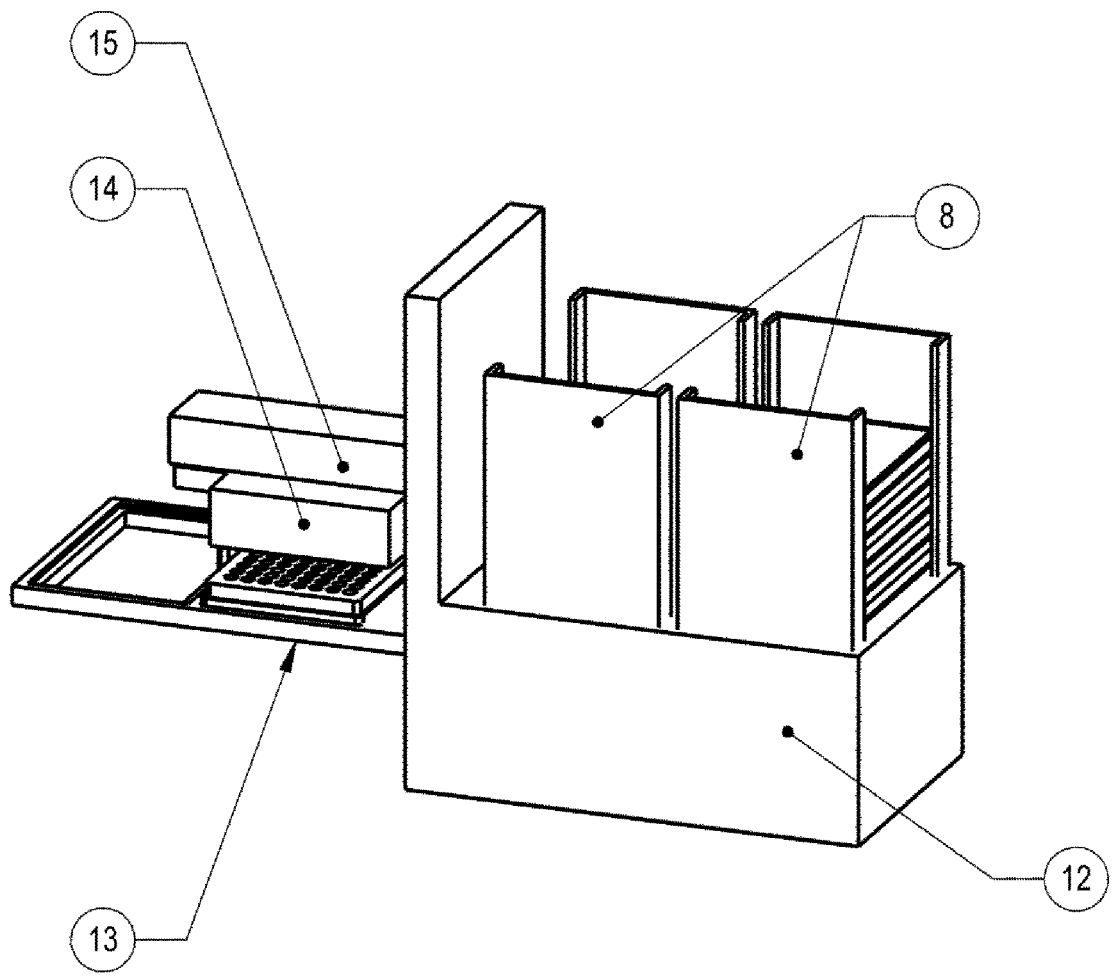
FIG. 12 is an oblique projection of a microplate stacker.

FIG. 12 illustrates a microplate stacker according to an embodiment.

As illustrated in FIG. 12, the microplate stacker includes a cassette 8, a main body unit 12, a carrier 13, a gripper 14, and an arm 15.

The cassette 8 includes a plurality of cassettes into which microplates are stacked. In FIG. 12, the cassette 8 includes a first cassette, which may be a source cassette, and a second cassette, which may be a destination cassette. The source cassette may store one or more unprocessed microplates and lids in a stack of unprocessed microplates and lids. The destination cassette may include one or more processed microplates and lids, which have undergone processing by a laboratory instrument, in a stack of processed microplates and lids.

The main body unit 12 includes internal components for removing microplates and lids from the source cassette and returning processed microplates and lids to the destination cassette.

The carrier 13 may be a conveyor belt, which conveys microplates and/or lids from a source cassette stack to one or more locations, such as a processing location at which the microplates and/or lids are processed by a laboratory instrument or a detection location at which a gripper may analyze whether a lid includes a microplate on top of the lid. Alternatively, the carrier 13 may convey microplates and/or lids to a location at which the gripper 14 and arm 15 may access the microplate and/or lid for transporting the microplate and/or lid to the processing location at which the microplate and/or lid may be processed by the laboratory instrument.

The gripper 14 and arm 15 may be components of an articulating robot that manipulates the microplates and/or lids conveyed by the carrier 13. The arm 15 may be positioned above and/or about a microplate and/or lid to select a microplate and/or lid. The gripper 14 may be articulated to select a microplate and/or lid, once positioning of the gripper 14 and arm 15 is complete.

FIGS. 13-26 illustrate operations of a microplate stacker, according to an embodiment.

Figure 27:
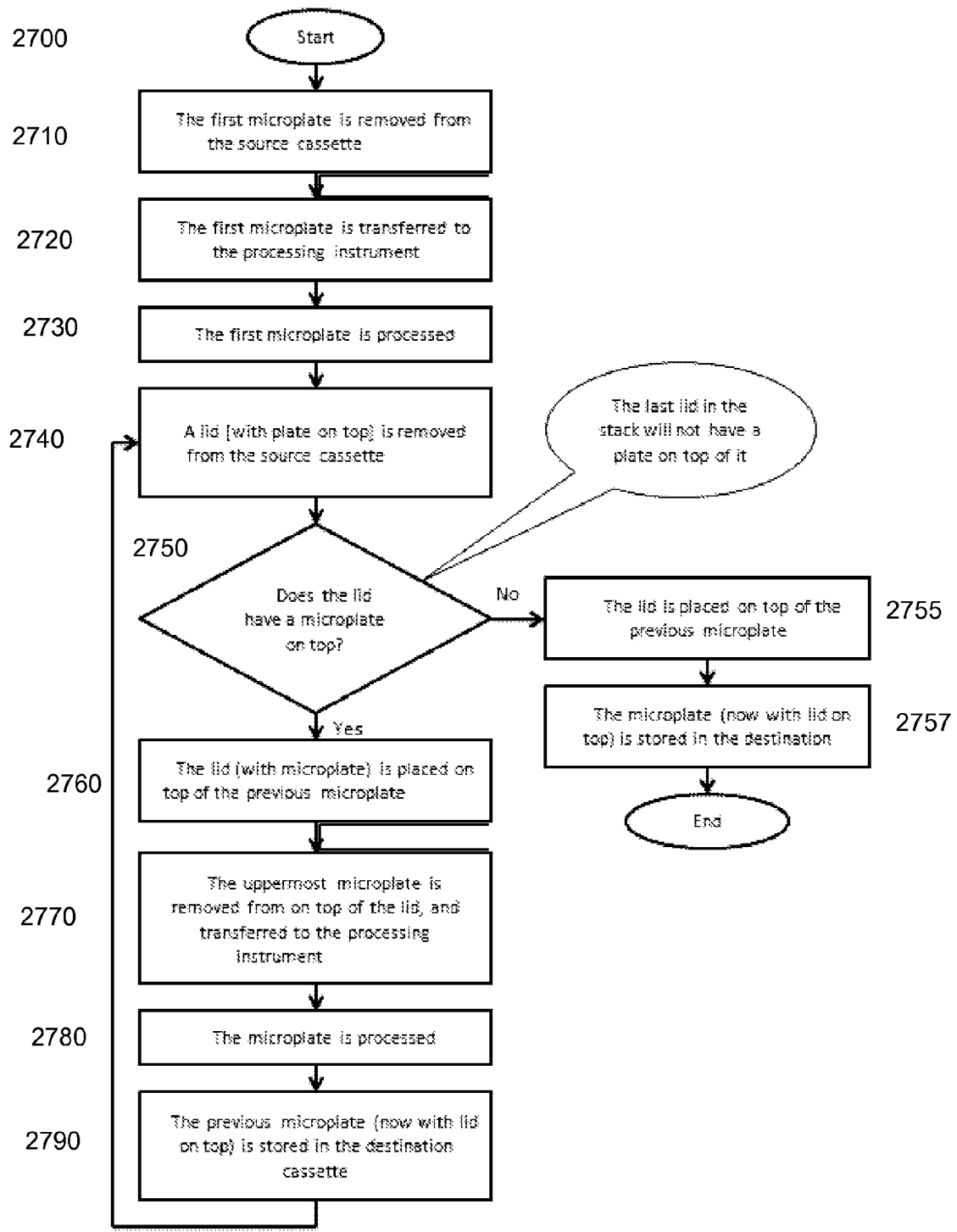
FIG. 27 is a flowchart of a method of processing microplates according to an embodiment.

FIG. 27 illustrates a flowchart of operations of a microplate stacker, according to an exemplary embodiment.

For ease of description and better understanding, the flowchart of FIG. 27 will be discussed with reference to FIGS. 13-26.

Figure 13:
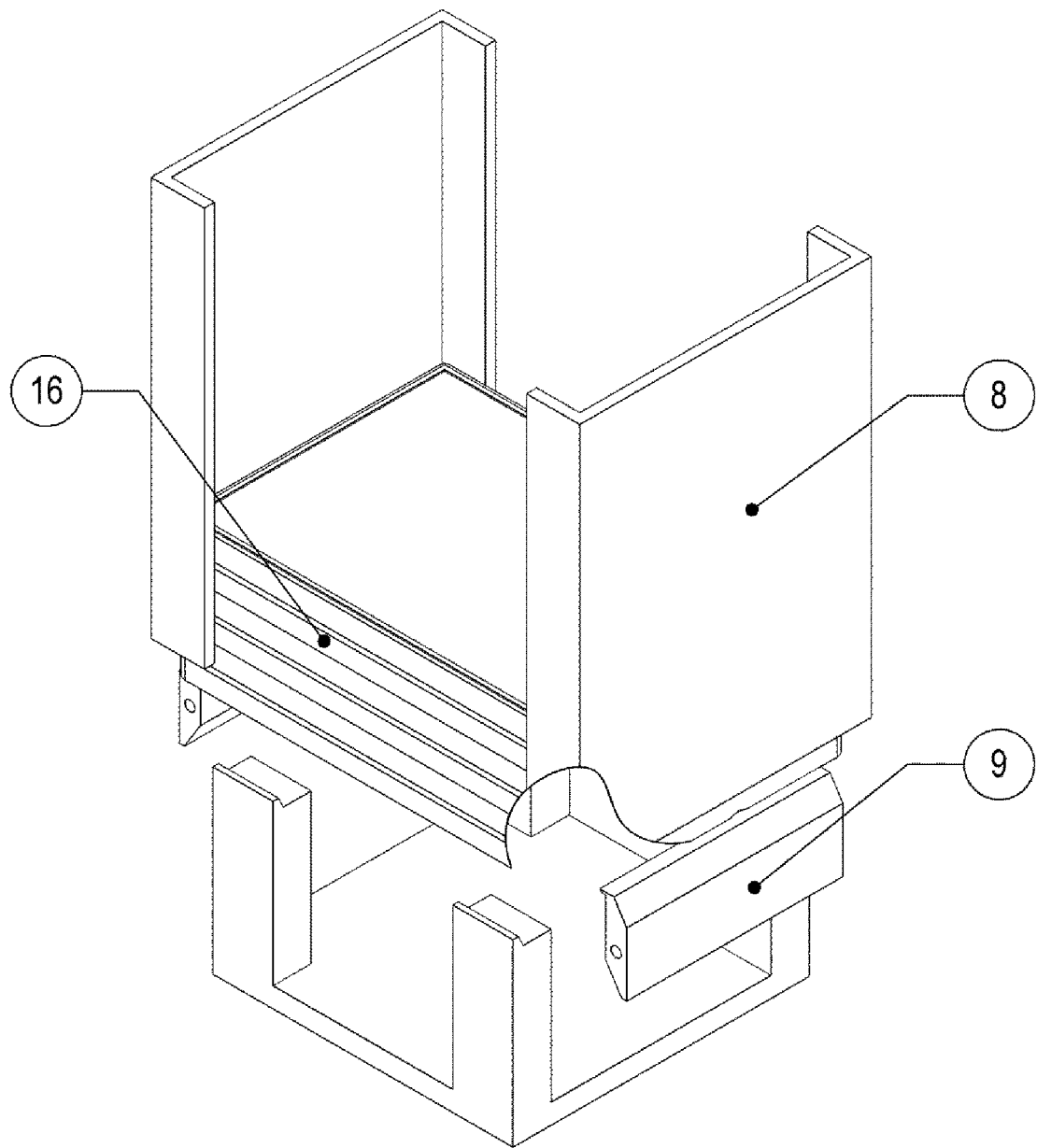
FIG. 13 is an isometric projection of a cassette with a stack of microplates, as used in a microplate stacker, according to an embodiment.

In operation 2700, a stack of microplates and lids 16 is loaded into a cassette 8 of the stacker. The stack of microplates and lids 16 may rest upon support features 9 located at the base of the cassette 8. FIG. 13 illustrates an isometric projection of a cassette 8 with a stack of microplates and lids 16, and FIG. 14 is an orthographic projection of the cassette 8 and stack of microplates and lids 16.

Figure 14:
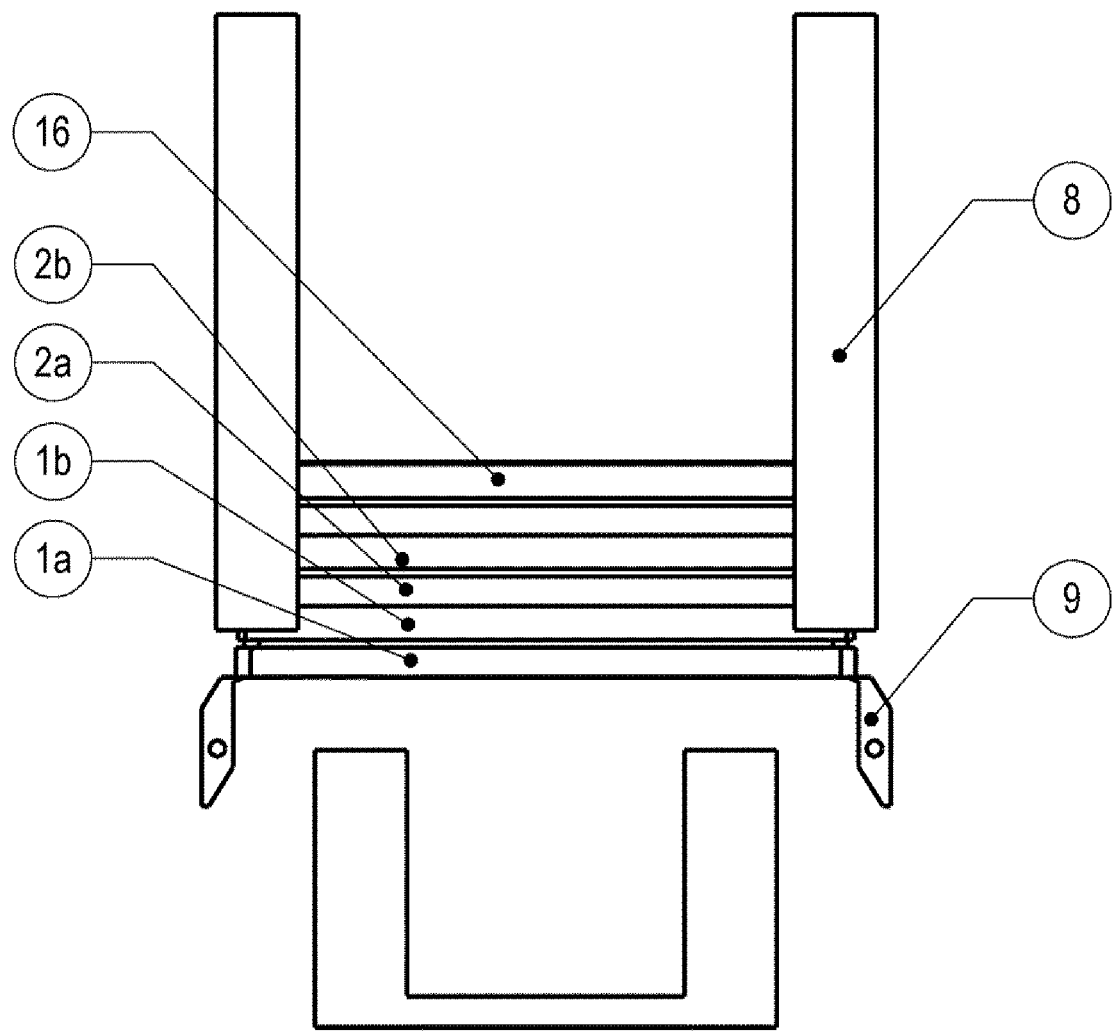
FIG. 14 is an orthographic projection of the cassette and stack of microplates from FIG. 13, according to an embodiment.

As illustrated in FIG. 14, the stack of microplates and lids 16 may include a lowermost microplate 1$a$ and corresponding lid 1$b$ on top of the lowermost microplate 1$a$. The stack of microplates and lids 16 may further include a next lowermost microplate 2$a$ and corresponding lid 2$b$ on top of the next lowermost microplate 2$a$.

The corresponding lid 1$b$ on top of the lowermost microplate 1$a$ acts as a base for the next lowermost microplate 2$a$, which is disposed on top of the lid 1$b$ of the lowermost microplate 1$a$. The corresponding lid 2$b$ of the next lowermost microplate 2$a$ is disposed on top of the next lowermost microplate 2$a$.

Naturally, more than two microplates and their corresponding lids may be disposed in the stack of microplates and lids 16, but only two microplates 1$a$, 1$b$ and their corresponding lids 2$a$, 2$b$ are individually illustrated for ease of description and understanding.

In operation 2710, lowermost microplate 1$a$ is removed from the stack of microplates 16.

Figure 15:
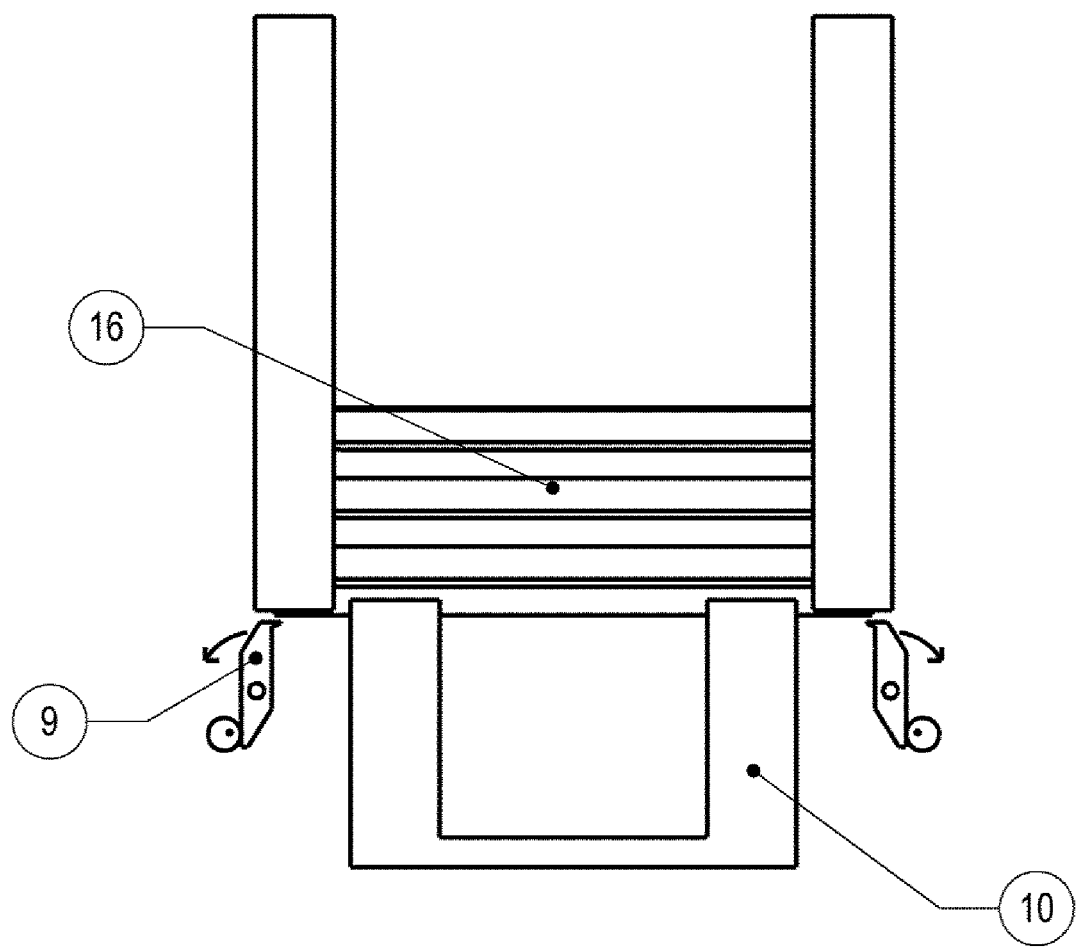
FIG. 15 is an orthographic projection of a cassette and stack of microplates with support features being retracted by a cam motion, according to an embodiment.

FIG. 15 is an orthographic projection of a cassette and stack of microplates with support features being retracted by a cam motion.

Specifically, lift mechanism 10 lifts the lowermost microplate 1$a$, and thus all microplates and lids in the stack of microplates and lids 16, off the support features 9. The lift mechanism 10 lifts the stack of microplates and lids 16 a distance sufficient to permit retraction of the support features 9. Once the lift mechanism 10 has lifted the stack of microplates and lids 16 off the support features 9, the support features 9 are retracted. The support features 9 may be retracted by cam motion or any actuating mechanism, motor, etc. through any programmable motion under control of a control mechanism.

Figure 16:
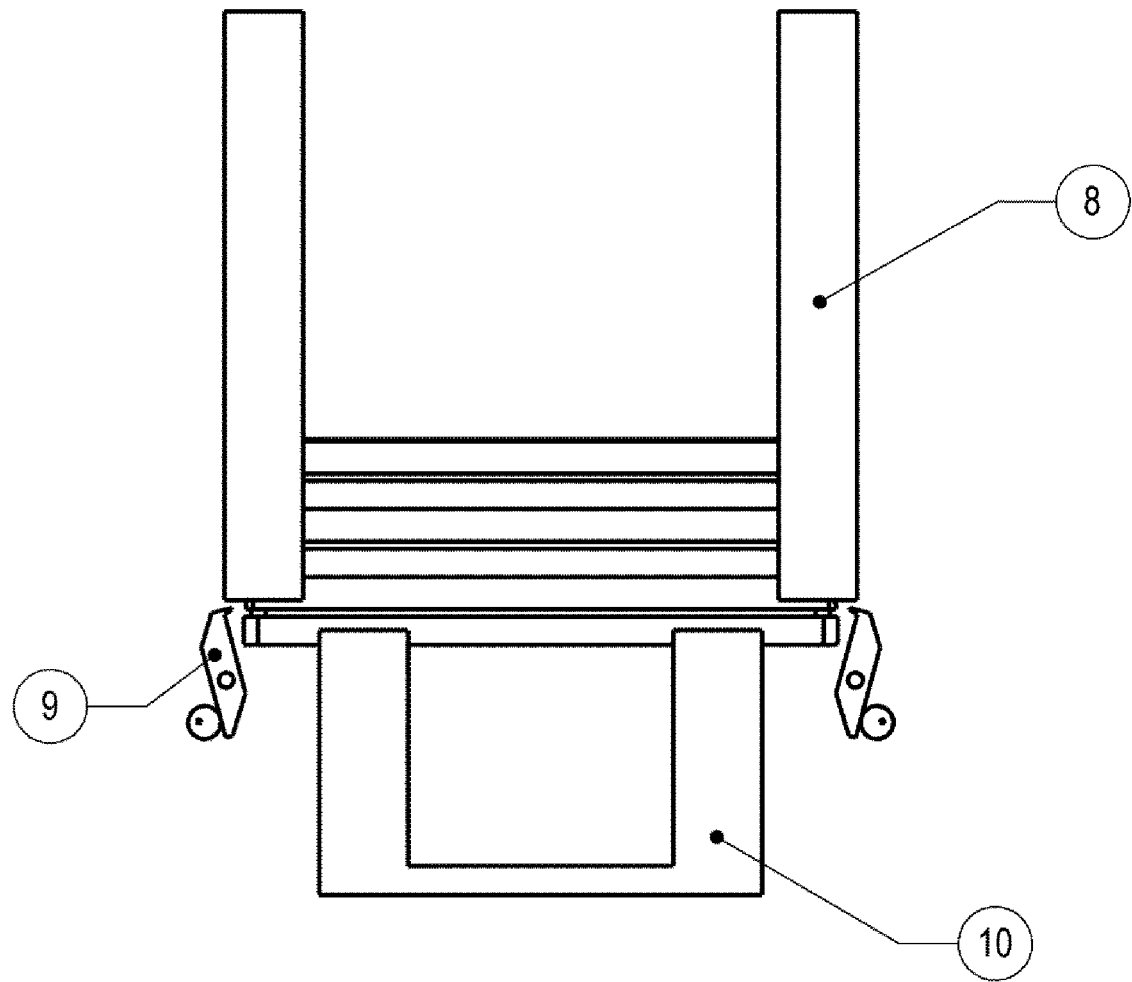
FIG. 16. Is an orthographic projection of a cassette and stack of microplates, with a lift mechanism lowering the microplate stack until a gap between the lower-most microplate and its lid is aligned with support features, according to an embodiment.

FIG. 16. is an orthographic projection of a cassette and stack of microplates, with a lift mechanism lowering the microplate stack until a gap between the lower-most microplate and its lid is aligned with support features.

As illustrated in FIG. 16, the lift mechanism 10 is lowered a predetermined distance such that the support features 9 are aligned with a gap that exists between the bottommost microplate 1$a$ and the corresponding lid 1$b$ of the bottommost microplate 1$a$. The distance the lift mechanism lowers the stack may be a programmed distance based on characteristics of the microplates and lids loaded into the cassette 8.

Figure 17:
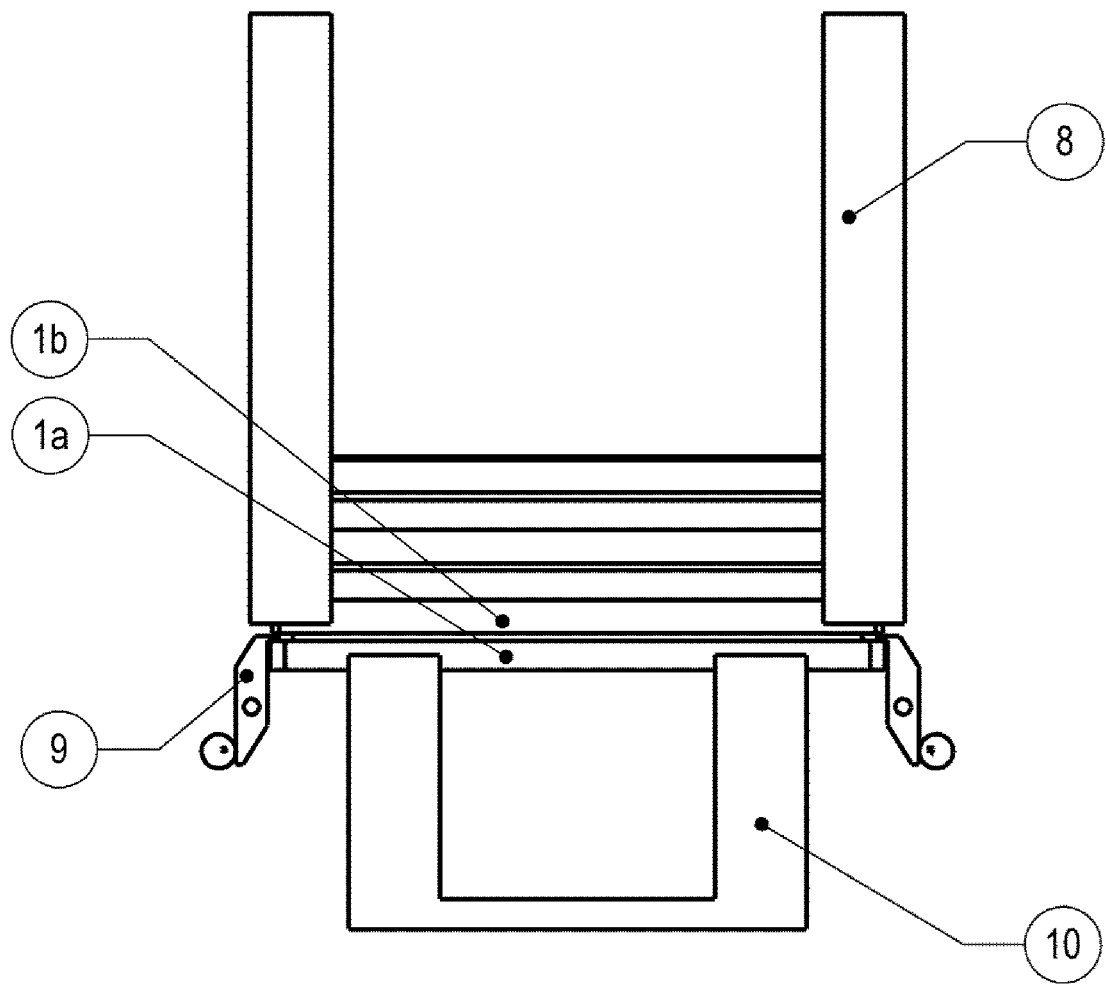
FIG. 17. Is an orthographic projection of a cassette and stack of microplates, the support features extended into a gap between the lower-most microplate and its lid, according to an embodiment.

FIG. 17. Is an orthographic projection of a cassette and stack of microplates, the support features extended into a gap between the lowermost microplate 1$a$ and the lid 1$b$ of the lowermost microplate 1$a$.

As illustrated in FIG. 17, once the support features 9 are positioned by the lift mechanism 10, the support features 9 are extended into the gap between the lowermost microplate 1$a$ and the lid 1$b$ of the lowermost microplate 1$a$.

Figure 11:
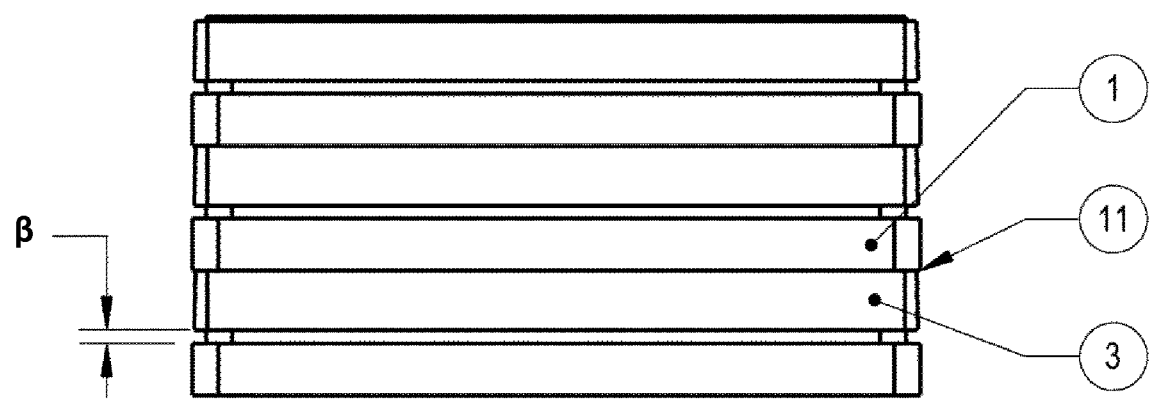
FIG. 11 illustrates a stack of conventional microplates and lids.

The gap ($\beta$) between the lowermost microplate 1$a$ and the lid 1$b$ of the lowermost microplate 1$a$ is typically about 1 mm or greater, as illustrated in FIG. 11.

Figure 18:
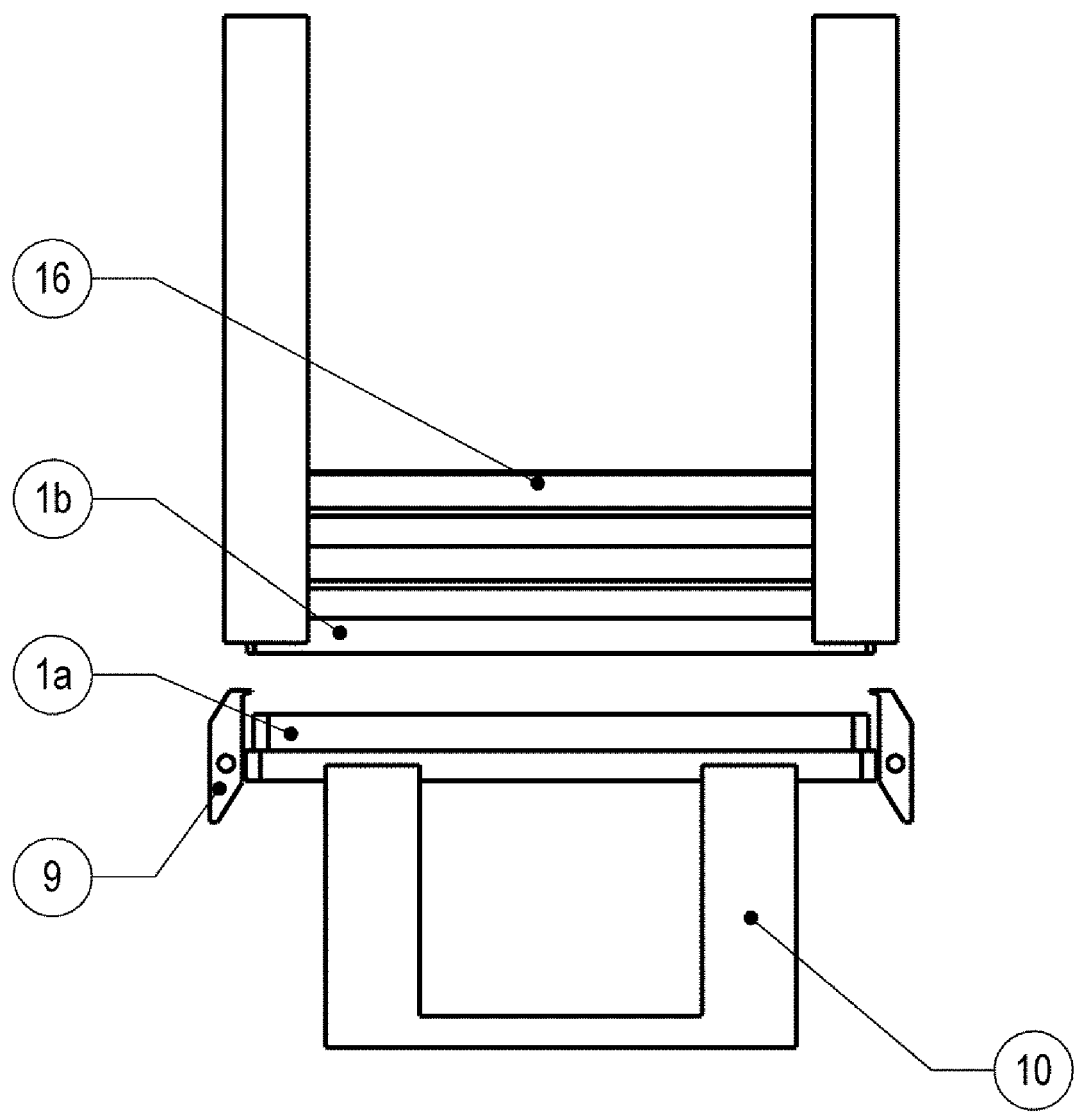
FIG. 18 is an orthographic projection of a cassette and stack of microplates, with a lift mechanism lowering the lower-most microplate from the stack, according to an embodiment.

FIG. 18 is an orthographic projection of a cassette and stack of microplates, with a lift mechanism lowering the lower-most microplate from the stack.

As illustrated in FIG. 18, the lift mechanism 10 is lowered. Accordingly, the lowermost microplate 1$a$ is lowered and separated from the stack of microplates 16, while the balance of microplates and lids remain in the stack of microplates and lids 16 due to support by the support features 9.

At this time, the corresponding lid 1$b$ of the bottommost microplate 1$a$ rests on the support features 9, and remains in the cassette 8.

Figure 19:
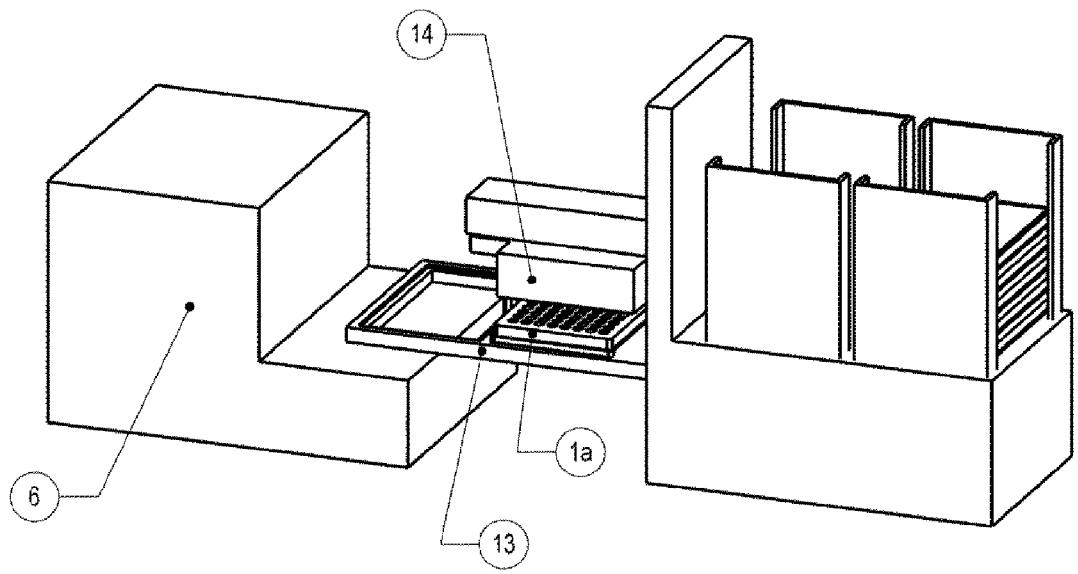
FIG. 19 is an oblique projection of a microplate stacker, interfaced with a laboratory instrument, according to an embodiment.
Figure 20:
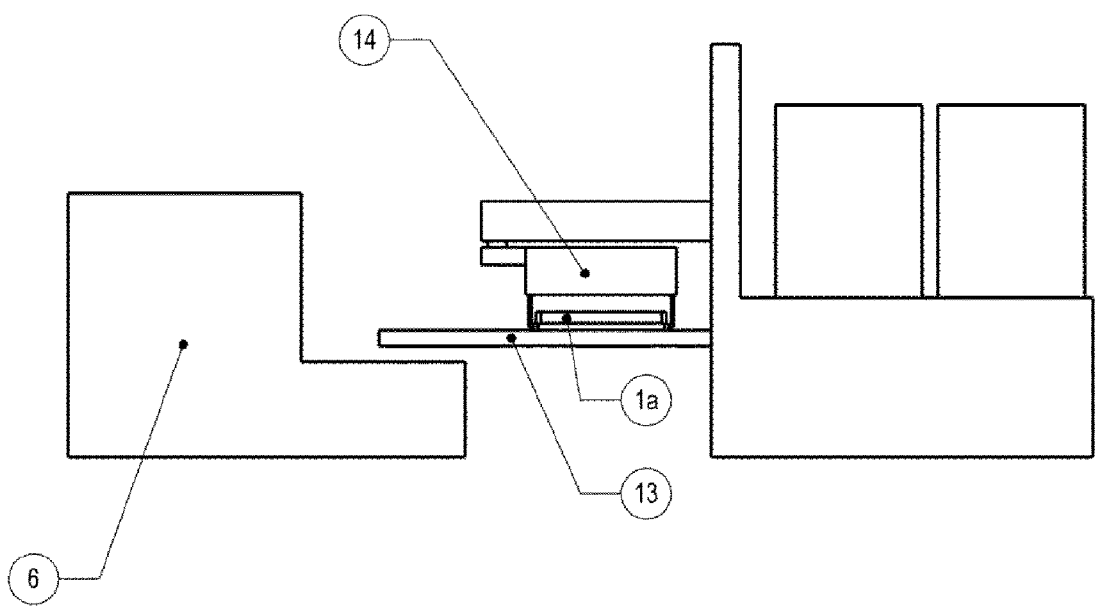
FIGS. 20-21 are orthographic projections of the microplate stacker from FIG. 19 loading a microplate to a laboratory instrument, according to an embodiment.
Figure 21:
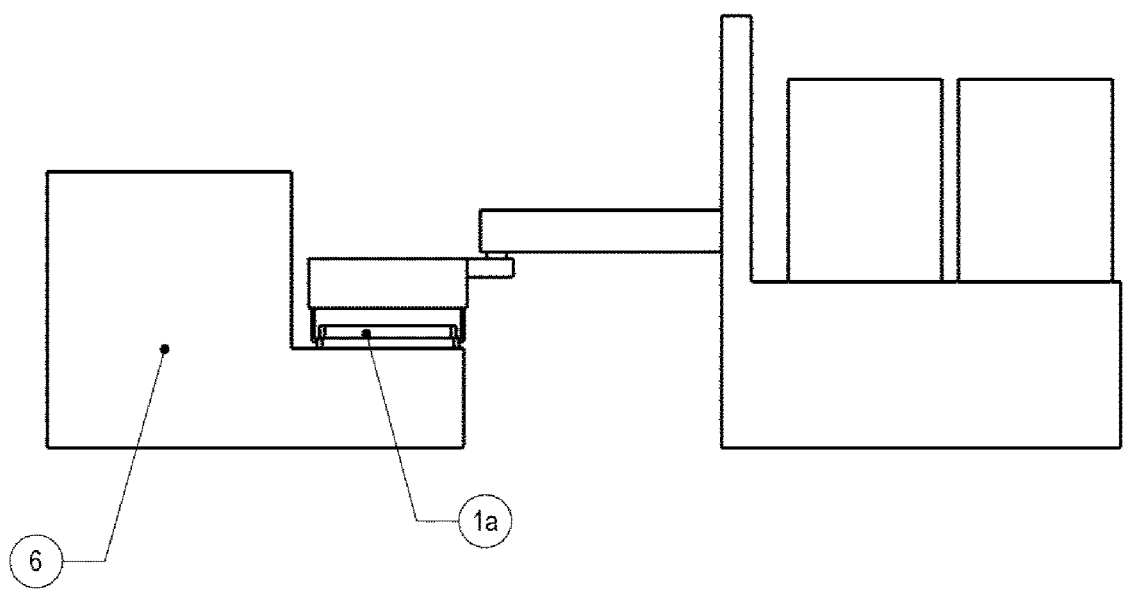

FIG. 19 is an oblique projection of a microplate stacker, interfaced with a laboratory instrument. FIGS. 20-21 are orthographic projections of the microplate stacker from FIG. 19 loading a microplate to a laboratory instrument, or in reverse order retrieving a microplate from a laboratory instrument.

In operation 2720, once removed from the stack of microplates and lids 16, the microplate 1$a$ is passed to an attached laboratory instrument 6 through any combination of carriers 13, articulating robots (arm 14 and gripper 15), etc., as illustrated in FIGS. 19-21.

As illustrated in FIG. 19, the gripper 14 may include fingers, which may be actuated to grip and release a microplate, a lid, or any combination of a microplate and a lid.

The gripper 14 may further include a sensor, such as an optical sensor or pressure sensor, for detecting presence of a plate or lid between the fingers. The optical sensor may detect presence of a plate or lid between the fingers when the optical sensor trips, or fails to trip, depending on implementation. The pressure sensor may sense pressure or resistance of the fingers due to presence of a plate or lid between the fingers. In operation 2730, the microplate 1$a$ is processed by the processing instrument.

As illustrated in FIG. 21, once the microplate 1$a$ is processed by the processing instrument, the microplate 1$a$ may be retrieved from the processing instrument and repositioned on the conveyor 13 by the gripper 14.

Figure 22:
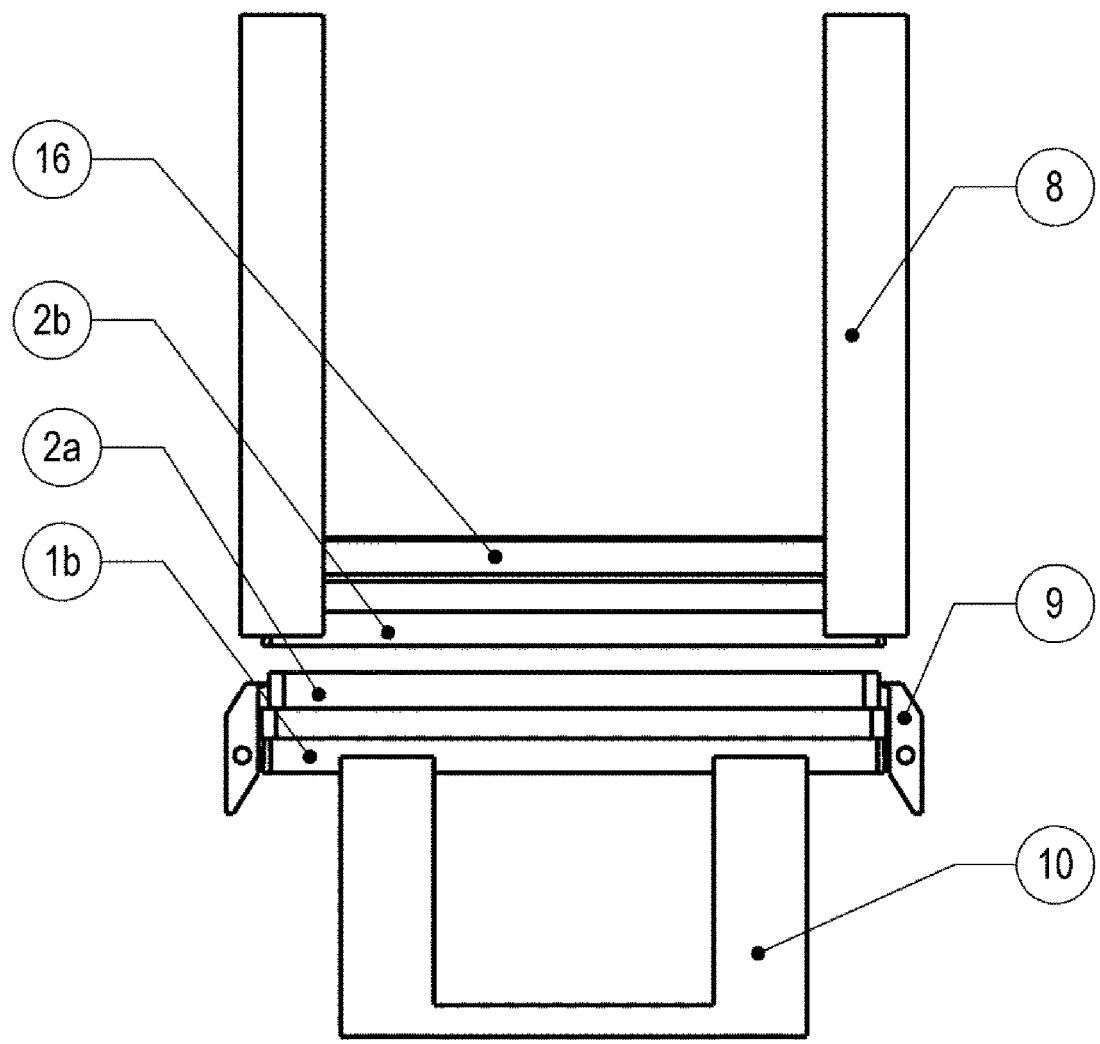
FIG. 22 is an orthographic projection of a cassette and stack of microplates, illustrating the removal of a microplate on top of a lid, according to an embodiment.

FIG. 22 is an orthographic projection of a cassette and stack of microplates, illustrating the removal of a microplate on top of a lid.

Specifically, in operation 2740, the stack of microplates and lids 16 may include a corresponding lid 1$b$ of the lowermost microplate 1$a$ and a next lowermost microplate 2$a$ on top of the corresponding lid 1$b$ of the lowermost microplate 1$a$, as illustrated in FIG. 22.

The lift mechanism 10 lifts the corresponding lid 1$b$ of the lowermost microplate 1$a$, and thus all microplates in the stack of microplates and lids 16, off the support features 9. The lift mechanism 10 lifts the stack of microplates and lids 16 a distance sufficient to permit retraction of the support features 9. Once the lift mechanism 10 has lifted the stack of microplates and lids 16, the support features 9 are retracted. The support features 9 may be retracted by cam motion or any actuating mechanism, motor, etc. through any programmable motion under control of a control mechanism.

The lift mechanism 10 is lowered a predetermined distance such that the support features 9 are aligned with a gap that exists between the next lowermost microplate 2$a$ and the corresponding lid 2$b$ of the next lowermost microplate 2$a$. The distance the lift mechanism 10 lowers the stack of microplates and lids 16 may be a programmed distance based on characteristics of the microplates and lids loaded into the cassette 8.

Once the support features 9 are positioned by the lift mechanism 10, the support features 9 are extended into the gap between the next lowermost microplate 2a and the lid 2b of the lowermost microplate 2a.

The gap between the next lowermost microplate 2a and the lid 2b of the next lowermost microplate 2b is typically about 1 mm or greater.

The lift mechanism 10 is lowered. Accordingly, the corresponding lid 1b of the lowermost microplate 1a and the next lowermost microplate 2a are lowered and separated from the stack of microplates 16, while the balance of microplates and lids remain in the stack of microplates 16 due to support by the support features 9.

Once removed from the stack of microplates 16, the corresponding lid 1b of the lowermost microplate 1a and the next lowermost microplate 2a, which is disposed on top of the lid 1b of the lowermost microplate 1a, may be conveyed to a detection position.

At operation 2750, it may be determined whether lid 1b of the lowermost microplate 1a includes a microplate disposed on top, namely the next lowermost microplate 2a.

Figure 23:
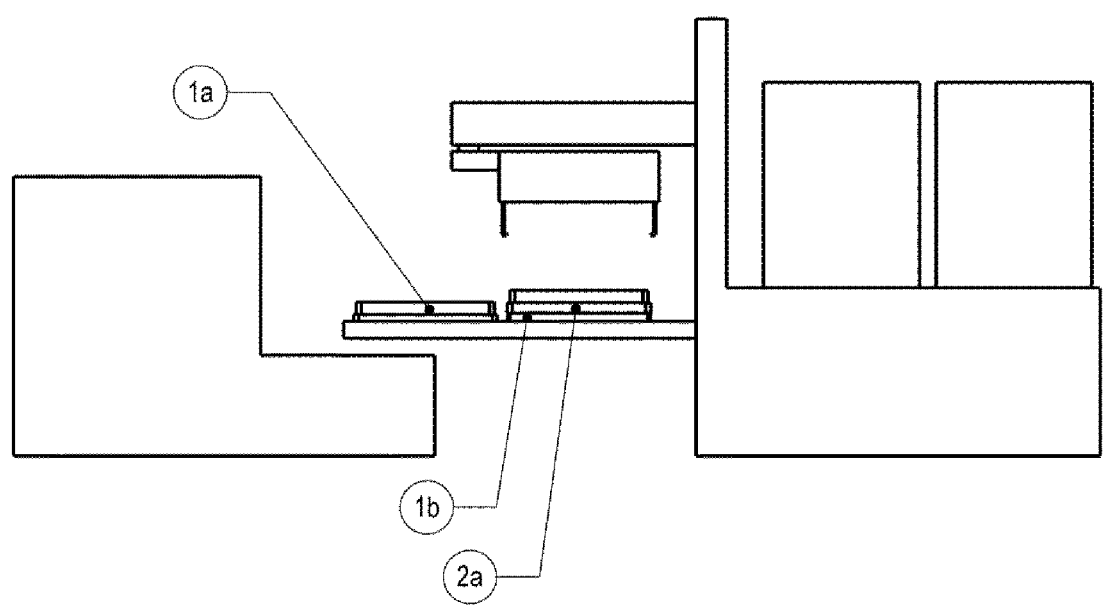
FIGS. 23-26 are orthographic projections illustrating how the lid of the first microplate is replaced, and the second microplate is prepared for processing, according to an embodiment
Figure 24:
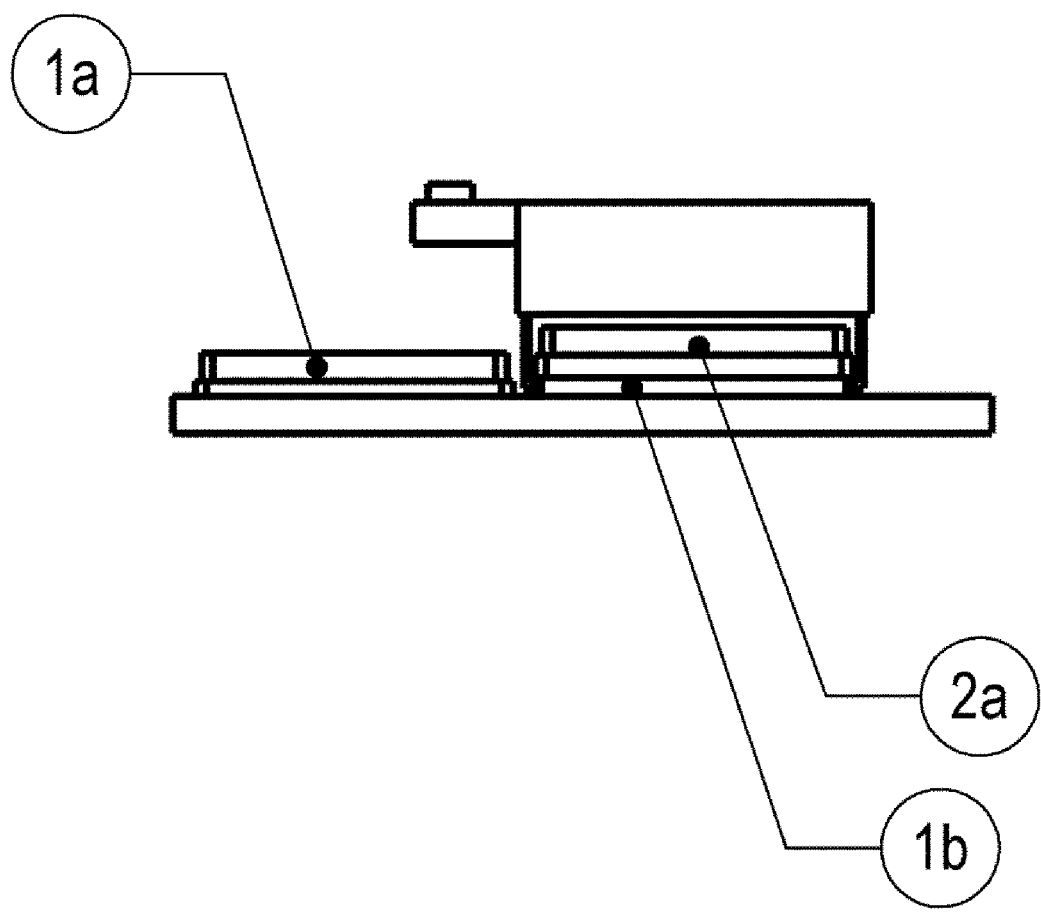

As illustrated in FIGS. 23-24, a gripping motion may be performed when a microplate is disposed on top of a lid. The gripping motion may be controlled by any actuating mechanism or controller. Presence or absence of the microplate may be detected using, for example an optical sensor. Alternatively, presence may be detected by resistance detected from attempting to grip a position at which a microplate or lid is disposed.

Once the lid 1b has been conveyed from the cassette 8, presence of a microplate on top of a lid may be detected. Accordingly, if a microplate is detected on top of a lid, the microplate may be removed.

A gripping motion may be performed at a position. For example, only a lid may be disposed at a position below the gripper. The gripper attempts to grip a position above the lid. Having not detected a microplate, it may be determined that no microplate is present at the position of the gripper.

Once it is determined that no microplate is present, the gripper 14 may be positioned about the lid. Again, the gripper 14 may perform a gripping motion and detect presence of the lid.

As a result, by using the gripper 14, presence of a microplate, a lid, a combination of a microplate on top of a lid, or combination of microplate and lid may be detected based on detected presence of an object and a height of the gripper.

As discussed above, the gripper may attempt to grip a position above the lid 1b of the lowermost microplate 1a. Here, presence of the next lowermost microplate 2a on top of the lid 1b of the lowermost microplate 1a may be detected.

Figure 25:
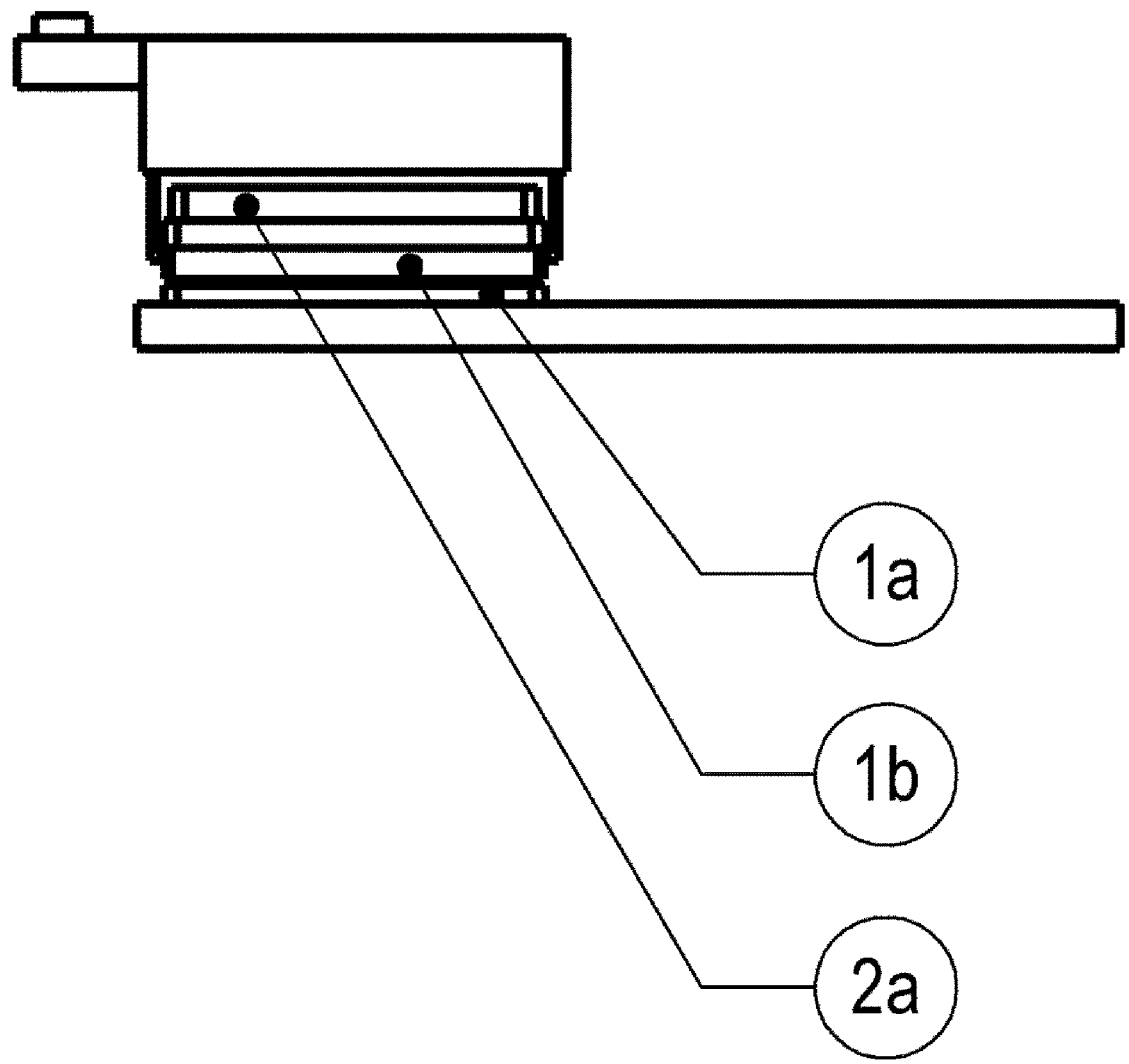
Figure 26:
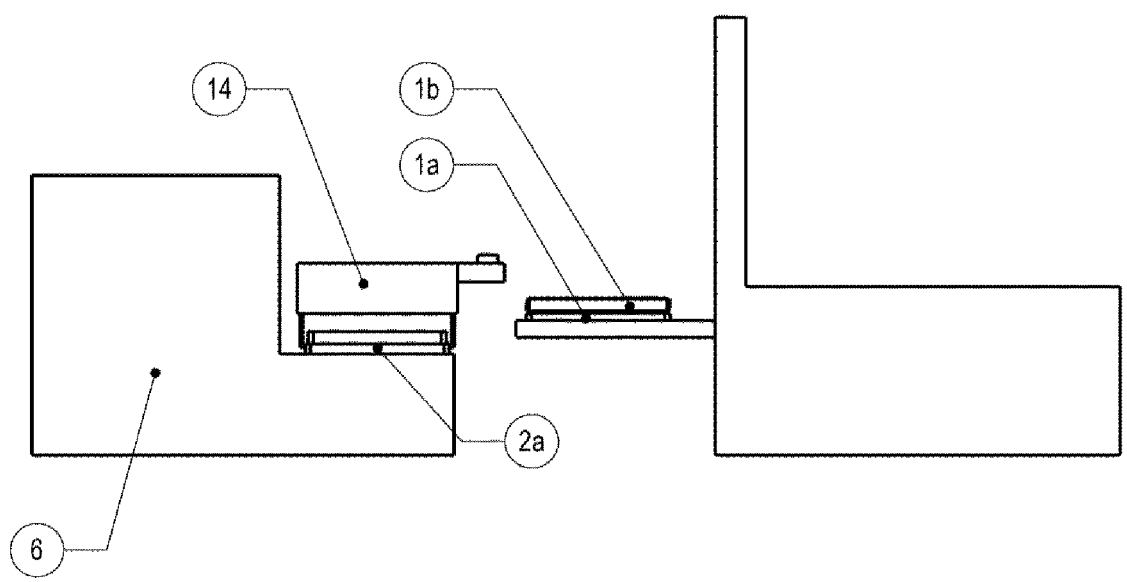

FIGS. 24-26 are orthographic projections illustrating how the lid of the first microplate is replaced, and the second microplate is prepared for processing.

As illustrated in FIG. 24, having detected presence of lowermost microplate 2a on top of the lid 1b of the lowermost microplate 1a, the gripper may select the lid 1b of the lowermost microplate 1a and the next lowermost microplate 2a from the conveyor.

In operation 2760, the gripper 14, having obtained the lid 1b of the lowermost microplate 1a and the next lowermost microplate 2a, may be positioned above the lowermost microplate 1a, and then lowered on top of the lowermost microplate 1a, as illustrated in FIG. 25.

Accordingly, the lowermost microplate 1a may now have disposed on top of itself the lid 1b of the lowermost microplate 1a and the next lowermost microplate 2a.

As illustrated in FIG. 26, in operation 2770, the gripper may be positioned and actuated to select the next lowermost microplate 2a. Therefore, the lowermost microplate 1a may now have disposed on top only the lid 1b of the lowermost microplate 1a. The next lowermost microplate 2a may be transferred to the processing instrument by the gripper 14.

In operation 2780 the next lowermost microplate 2a may be processed by the processing instrument.

In operation 2790, the processed microplate 1a and lid 1b may be conveyed by conveyor to the destination stack of the stacker. Accordingly, the processed microplate 1a and lid 1b may be stacked in the destination stack of the stacker.

Alternatively, at operation 2750, it may be determined that a lid does not include a microplate disposed on top. For example, a last lid in the cassette will not have a next microplate disposed on top in the cassette.

In operation 2755, if it is determined that a lid does not include a microplate disposed on top, the lid is placed on top of a processed microplate.

In operation 2757, the processed microplate with lid are conveyed by conveyor to the destination stack of the stacker. Accordingly, all microplates in the cassette are processed and transferred to the destination stack of the stacker.

Figure 28:
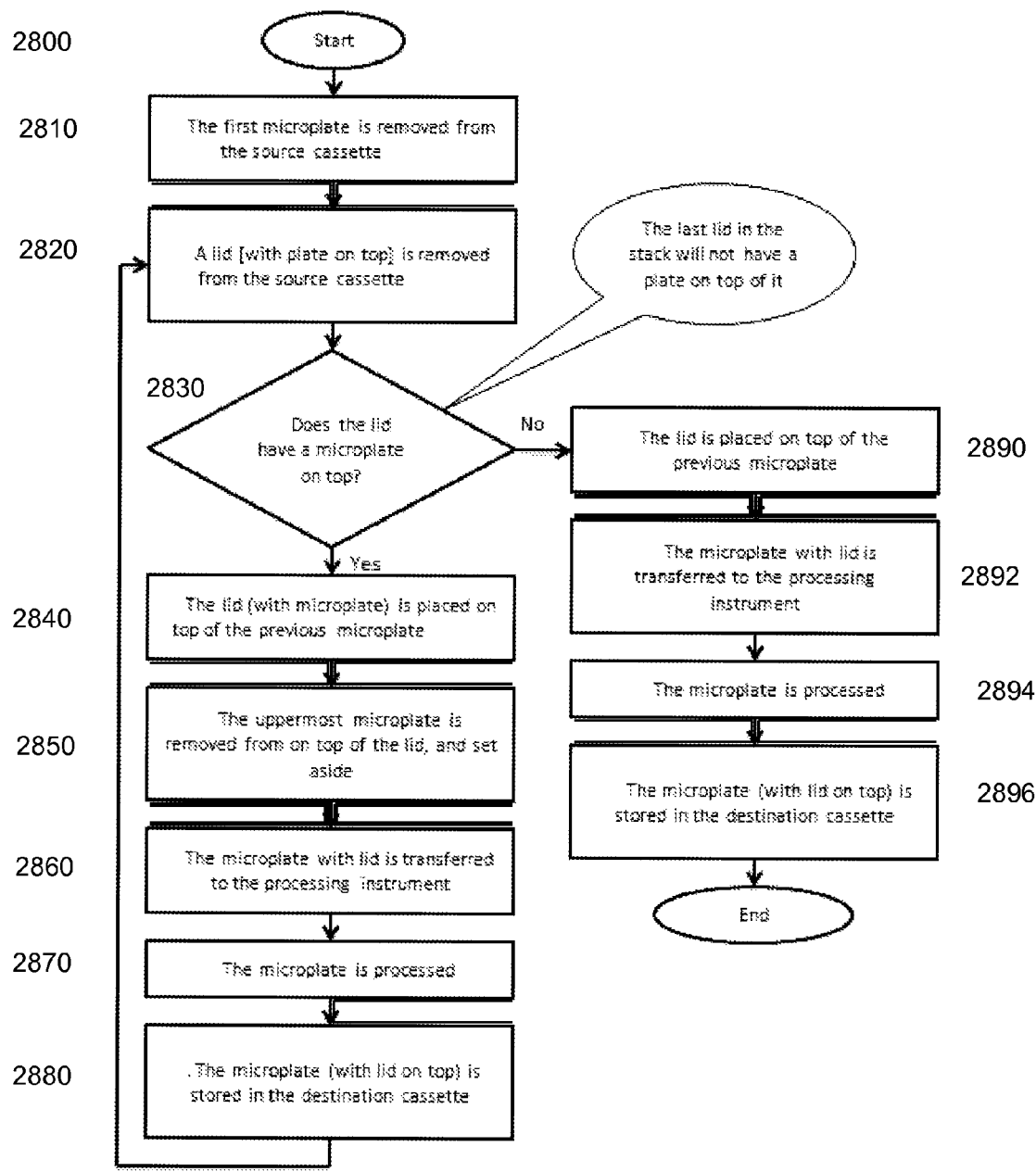
FIG. 28 is a flowchart of a method of processing microplates according to an embodiment.

FIG. 28 is a flowchart of a method of processing microplates according to an embodiment.

FIG. 28 differs from the flowchart of FIG. 27 in that a microplate is processed, using an attached instrument, along with its corresponding lid, whereas a microplate in FIG. 27 is processed, using an attached instrument, without its corresponding lid.

In operation 2800, a stack of microplates and lids 16 is loaded into a cassette 8 of the stacker. The stack of microplates and lids 16 may rest upon support features 9 located at the base of the cassette 8.

In operation 2810, a lowermost microplate is removed from the stack of microplates.

In operation 2820, a lid with a next microplate on top of the lid is removed from the source cassette.

In operation 2830, it is determined whether the lid includes a microplate on top of the lid. The last lid in the source cassette will not have a microplate on top of the last lid.

In operation 2840, in response to determining that a microplate exists on top of the lid, the lid and microplate are placed on top of a processed microplate, which was previously removed from the source stack and processed at the processing instrument. Accordingly, a processed microplate now includes its corresponding lid on top of the processed microplate, and a next microplate is positioned on top of the lid of the processed microplate.

In operation 2850, the next microplate on top of the processed microplate is removed from the top of the lid. The next microplate is set aside, to a holding position.

In operation 2860, the microplate with its corresponding lid is transferred to a processing location at the processing instrument.

In operation 2870, the microplate with its corresponding lid are processed at the processing instrument.

In operation 2880, the processed microplate with its corresponding lid are stored in a destination stack.

In operation 2890, if it is determined that the lid does not have a microplate on top in operation 2830, then it is determined that the lid is the last item in the source stack. The lid is then placed on top of its microplate, which has not been processed.

In operation 2892, the microplate with lid on top is transferred to a processing location at a processing instrument.

In operation 2894, the microplate with lid on top is processed by the processing instrument.

In operation 2896, the processed microplate with its corresponding lid are stored in the destination stack.

According to embodiments discussed above, lids are removed (de-lidded) from microplates. While there is no gap between the lid of the lowermost microplate and the microplate above it, there is a small gap between the flange of the microplate and the lid belonging to that microplate. A narrow microplate support feature is inserted into this gap thereby removing only the lowermost microplate, while the lid is retained within the cassette. The microplate is passed to an attached laboratory instrument. The process is repeated to remove the next microplate, which will consist of the lid of the previous microplate, with the next microplate on top of it.

After the microplate is returned from the laboratory instrument, the lid and next microplate are moved together and placed on top of processed microplate. The next microplate is moved from on top of the lid, and delivered to the attached laboratory instrument for processing. The microplate, with lid, is now able to be moved via a lift mechanism into a second "output" stack within the stacker. The process above is repeated until all microplates have been processed.

According to embodiments, it may be possible the microplates are processed on the attached laboratory instrument with their lids in place. The sequence previously described is conducted, but the microplate is passed to the laboratory instrument only after its corresponding lid is in place.

The methods for controlling microplate processing according to the above-described various embodiments may be implemented using computer-executable program code and may be stored in various non-transitory computer readable media, and may be executed by a processor. Accordingly, the processor may control components of a stacker system to implement the microplate processing.

The non-transitory computer readable medium refers to a medium that stores data semi-permanently, rather than storing data for a very short time, such as a register, a cache, and a memory, and is readable by an apparatus, such as the stacker. Specifically, the above-described various applications or programs may be stored in a non-transitory computer readable medium such as a compact disc (CD), a digital versatile disk (DVD), a hard disk, a Blu-ray disk, a universal serial bus (USB) memory stick, a memory card, and a read only memory (ROM), hard disk, random access memory (RAM) and may be provided.

What is claimed is:

1. A microplate stacker comprising:
   a cassette stack configured to retain a stack of a plurality of microplates and a plurality of lids corresponding to the plurality of microplates;
   a lift mechanism configured to raise or lower the stack of the plurality of microplates and the plurality of lids;
   a stack dog comprising retractable supports configured to extend into a gap between a microplate amongst the plurality of microplates and a corresponding lid of the microplate amongst the plurality of lids;
   an actuating mechanism configured to extend the retractable supports of the stack dog into the gap between the microplate amongst the plurality of microplates and the corresponding lid of the microplate amongst the plurality of microplates; and
   a controller programmed to control the lift mechanism to position the stack of the plurality of microplates and the plurality of lids to a position at which the retractable supports are substantially aligned with the gap between the microplate amongst the plurality of microplates and the corresponding lid of the microplate amongst the plurality of microplates, control the actuating mechanism to extend the retractable supports of the stack dog into the gap between the microplate amongst the plurality of microplates and the corresponding lid of the microplate amongst the plurality of microplates, and control the lift mechanism to lower the microplate amongst the plurality of microplates to separate the microplate amongst the plurality of microplates from the corresponding lid of the microplate amongst the plurality of microplates once the actuating mechanism extends the retractable supports of the stack dog into the gap between the microplate amongst the plurality of microplates and the corresponding lid of the microplate amongst the plurality of microplates.

2. The microplate stacker of claim 1, wherein the controller comprises:
   a memory programmed with computer-readable instructions to:
      control the lift mechanism to position the stack of the plurality of microplates and the plurality of lids to a position at which the retractable supports are substantially aligned with the gap between the microplate and the corresponding lid of the microplate;
      control the actuating mechanism to extend the retractable supports of the stack dog into the gap between the microplate and the corresponding lid of the microplate;
      and control the lift mechanism to lower the microplate to separate the microplate from the corresponding lid of the microplate once the actuating mechanism extends the retractable supports of the stack dog into the gap between the microplate and the corresponding lid of the microplate; and
   a processor configured to execute the computer-readable instruction.

3. The microplate stacker of claim 1, wherein the actuating mechanism is further configured to retract the retractable supports of the stack dog from contact with the microplate and the corresponding lid of the microplate.

4. The microplate stacker of claim 1, wherein the retractable supports are configured to support one or more of the plurality of microplates and one or more of the plurality of lids.

5. The microplate stacker of claim 1, wherein a width of the gap is 4 mm to 12 mm.

6. The microplate stacker of claim 1, wherein the cassette stack comprises the stack of the plurality of microplates and the plurality of lids corresponding to the plurality of microplates.

7. A method of using a microplate stacker to manipulate a stack of a plurality of microplates and a plurality of lids corresponding to the plurality of microplates, wherein the microplate stacker comprises:
   a cassette stack configured to retain the stack of a plurality of microplates and the plurality of lids corresponding to the plurality of microplates;
   a lift mechanism configured to raise or lower the stack of the plurality of microplates and the plurality of lids;
   a stack dog comprising the retractable supports configured to extend into a gap between a microplate in the plurality of microplates and a corresponding lid of the microplate in the plurality of microplates;
   an actuating mechanism configured to extend the retractable supports of the stack dog into the gap between the microplate in the plurality of microplates and the corresponding lid of the microplate in the plurality of microplates; and a controller programmed to control the lift mechanism to position the stack of the plurality of microplates and the plurality of lids to a position at which the retractable supports are substantially aligned with the gap between the microplate amongst the plurality of microplates and the corresponding lid of the microplate amongst the plurality of microplates, control the actuating mechanism to extend the retractable supports of the stack dog into the gap between the microplate amongst the plurality of microplates and the corresponding lid of the microplate amongst the plurality of microplates, and control the lift mechanism to lower the microplate amongst the plurality of microplates to separate the microplate amongst the plurality of microplates from the corresponding lid of the microplate amongst the plurality of microplates once the actuating mechanism extends the retractable supports of the stack dog into the gap between the microplate amongst the plurality of microplates and the corresponding lid of the microplate amongst the plurality of microplates;

the method comprising:

positioning the stack of the plurality of microplates and the plurality of lids to a position at which retractable supports are substantially aligned with a gap between a microplate amongst the plurality of microplates and a corresponding lid of the microplate amongst the plurality of lids;

extending retractable supports into the gap between the microplate amongst the plurality of microplates and the corresponding lid of the microplate amongst the plurality of microplates; and lowering the microplate amongst the plurality of microplates to separate the microplate amongst the plurality of microplates from the corresponding lid of the microplate amongst the plurality of microplates once the retractable supports are extended into the gap between the microplate amongst the plurality of microplates and the corresponding lid of the microplate amongst the plurality of microplates.

* * * * *